US010316289B2

(12) United States Patent
Gattinoni et al.

(10) Patent No.: US 10,316,289 B2
(45) Date of Patent: Jun. 11, 2019

(54) METHODS OF PRODUCING T MEMORY STEM CELL POPULATIONS

(75) Inventors: Luca Gattinoni, Washington, DC (US); Enrico Lugli, Bethesda, MD (US); Mario Roederer, Washington, DC (US); Nicholas P. Restifo, Chevy Chase, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 738 days.

(21) Appl. No.: 14/425,713

(22) PCT Filed: Sep. 6, 2012

(86) PCT No.: PCT/US2012/053947
§ 371 (c)(1),
(2), (4) Date: Jul. 6, 2015

(87) PCT Pub. No.: WO2014/039044
PCT Pub. Date: Mar. 13, 2014

(65) Prior Publication Data
US 2015/0299656 A1 Oct. 22, 2015

(51) Int. Cl.
*C12N 15/85* (2006.01)
*C12N 5/0783* (2010.01)
*A61K 35/17* (2015.01)
*A61K 39/00* (2006.01)

(52) U.S. Cl.
CPC ............ *C12N 5/0636* (2013.01); *A61K 35/17* (2013.01); *A61K 2039/5158* (2013.01); *A61K 2039/572* (2013.01); *C12N 2501/2302* (2013.01); *C12N 2501/415* (2013.01); *C12N 2501/51* (2013.01); *C12N 2501/515* (2013.01); *C12N 2501/727* (2013.01)

(58) Field of Classification Search
None
See application file for complete search history.

(56) References Cited

U.S. PATENT DOCUMENTS

| 7,820,174 | B2 | 10/2010 | Wang et al. |
| 8,034,334 | B2 | 10/2011 | Dudley et al. |
| 8,088,379 | B2 | 1/2012 | Robbins et al. |
| 8,216,565 | B2 | 7/2012 | Restifo et al. |
| 2005/0075276 | A1 | 4/2005 | Rudd |
| 2009/0304657 | A1 | 12/2009 | Morgan et al. |
| 2012/0244133 | A1 | 9/2012 | Rosenberg et al. |
| 2014/0101786 | A1* | 4/2014 | Sykes ............... A61K 49/0008 800/11 |
| 2016/0045580 | A1* | 2/2016 | Turtle ............... C12N 5/0636 424/209.1 |
| 2016/0222409 | A1* | 8/2016 | Baltimore ........ C07K 16/2887 |

FOREIGN PATENT DOCUMENTS

| WO | WO 9506409 | * | 3/1995 |
| WO | WO 2010/151517 A2 | | 12/2010 |
| WO | WO 2011/041093 A1 | | 4/2011 |
| WO | WO 2012/040012 A1 | | 3/2012 |
| WO | WO 2012/054825 A1 | | 4/2012 |
| WO | WO 2012/138475 A1 | | 10/2012 |

OTHER PUBLICATIONS

Alanio et al., "Enumeration of human antigen-specific naive CD8+ T cells reveals conserved precursor frequencies," *Blood*, 115 (18), 3718-3725 (2010).
Appay et al., "Phenotype and function of human T lymphocyte subsets: consensus and issues," *Cytometry A.*, 73 (11), 975-983 (2008).
Carpenito et al., "Control of large, established tumor xenografts with genetically retargeted human T cells containing CD28 and CD137 domains," *Proc. Natl. Acad. Sci. USA*, 106 (9), 3360-3365 (2009).
Cavalieri et al., "Human T lymphocytes transduced by lentiviral vectors in the absence of TCR activation maintain an intact immune competence," *Blood*, 102 (2), 497-505 (2003).
De Rosa et al., "11-color, 13-parameter flow cytometry: identification of human naive T cells by phenotype, function, and T-cell receptor diversity," *Nat. Med.*, 7 (2), 245-248 (2001).
Douek et al., "Changes in thymic function with age and during the treatment of HIV infection," *Nature*, 396 (6712), 690-695 (1998).
Dusseaux et al., "Human MAIT cells are xenobiotic-resistant, tissue-targeted, CD161hi IL-17-secreting T cells," *Blood*, 117 (4), 1250-1259 (2011).
Feng et al., "Transcription factor Foxp1 exerts essential cell-intrinsic regulation of the quiescence of naive T cells," *Nat. Immunol.*, 12 (6), 544-550 (2011), author manuscript.

(Continued)

*Primary Examiner* — Michail A Belyavskyi
(74) *Attorney, Agent, or Firm* — Leydig, Voit & Mayer Ltd.

(57) ABSTRACT

Provided are methods of producing an isolated T memory stem cell population, the method comprising a) isolating nave T cells from a mammal, wherein the mammal is not a mouse; b) activating the nave T cells and expanding the numbers of nave T cells in the presence of one or more non-specific T cell stimuli, one or more cytokines, and a GSK-3beta inhibitor. Also provided are methods of producing an isolated T memory stem cell population, the method comprising a) isolating lymphocytes from a mammal; b) sorting the lymphocytes using flow cytometry into a population comprising a phenotype comprising i) CD95+, CD45RO−, and CCR7+; and ii) CD62L+ or one or more of CD27+, CD28+, CD45RA+, and CD127+ to produce an isolated T memory stem cell population. Further embodiments of the invention provide related cells, populations of cells, pharmaceutical compositions, and methods of treating or preventing cancer.

12 Claims, 14 Drawing Sheets

(56) References Cited

OTHER PUBLICATIONS

Forget et al., "Stimulation of Wnt/β-catenin pathway in human CD8+ T lymphocytes from blood and lung tumors leads to a shared young/memory phenotype," *PLoS One*, 7 (7), e41074, 1-12 (2012).
Gattinoni et al., "A human memory T cell subset with stem cell-like properties," *Nat. Med.*, 17 (10), 1290-1298 (2011).
Gattinoni et al., "Acquisition of full effector function in vitro paradoxically impairs the in vivo antitumor efficacy of adoptively transferred CD8+ T cells," *J. Clin. Invest.*, 115 (6), 1616-1626 (2005).
Gattinoni et al., "Adoptive immunotherapy for cancer: building on success," *Nat. Rev. Immunol.*, 6 (5), 383-393 (2006), author manuscript.
Gattinoni et al., "Wnt signaling arrests effector T cell differentiation and generates CD8+ memory stem cells," *Nat. Med.*, 15 (7), 808-814 (2009).
Gattinoni et al., "Wnt/β-Catenin Signaling in T-Cell Immunity and Cancer Immunotherapy," *Clin. Cancer Res.*, 16 (19), 4695-4701 (2010).
Geginat et al., "Cytokine-driven proliferation and differentiation of human naive, central memory, and effector memory CD4(+) T cells," *J. Exp. Med.*, 194 (12), 1711-1719 (2001).
Geginat et al., "Proliferation and differentiation potential of human CD8+ memory T-cell subsets in response to antigen or homeostatic cytokines," *Blood*, 101 (11), 4260-4266 (2003).
Hinrichs et al., "Adoptively transferred effector cells derived from naive rather than central memory CD8+ T cells mediate superior antitumor immunity," *Proc. Natl. Acad. Sci. USA*, 106 (41), 17469-17474 (2009).
International Preliminary Report on Patentability, Application No. PCT/US2012/053947, dated Mar. 10, 2015.
International Search Report, Application No. PCT/US2012/053947, dated May 3, 2013.
Joshi et al., "Inflammation directs memory precursor and short-lived effector CD8(+) T cell fates via the graded expression of T-bet transcription factor," *Immunity*, 27 (2), 281-295 (2007).
June, "Adoptive T cell therapy for cancer in the clinic," *J. Clin. Invest.*, 117 (6), 1466-1476 (2007).
Kambayashi et al., "Memory CD8+ T cells provide an early source of IFN-gamma," *J. Immunol.*, 170 (5), 2399-2408 (2003).
Khan et al., "Gene expression profiling of alveolar rhabdomyosarcoma with cDNA microarrays," *Cancer Res.*, 58 (22), 5009-5013 (1998).
Klebanoff et al., "Central memory self/tumor-reactive CD8+ T cells confer superior antitumor immunity compared with effector memory T cells," *Proc. Natl. Acad. Sci. USA*, 102 (27), 9571-9576 (2005).
Lugli et al., "Identification, isolation and in vitro expansion of human and nonhuman primate T stem cell memory cells," *Nat. Protoc.*, 8 (1), 33-42 (2013).
Lugli et al., "Quercetin inhibits lymphocyte activation and proliferation without inducing apoptosis in peripheral mononuclear cells," *Leuk. Res.*, 33 (1), 140-150 (2009).
Lugli et al., "Transient and persistent effects of IL-15 on lymphocyte homeostasis in nonhuman primates," *Blood*, 116 (17), 3238-3248 (2010).
Mahnke et al., "Optimizing a multicolor immunophenotyping assay," *Clin. Lab. Med.*, 27 (3), 469-485 (2007), author manuscript.
Morgan et al., "Cancer regression in patients after transfer of genetically engineered lymphocytes," *Science*, 314 (5796), 126-129 (2006), author manuscript.

Muralidharan et al., "Activation of Wnt Signaling Arrests Effector Differentiation in Human Peripheral and Cord Blood-Derived T Lymphocytes," *J. Immunol.*, 187 5221-5232 (2011).
Oberdoerffer et al., "Regulation of CD45 alternative splicing by heterogeneous ribonucleoprotein, hnRNPLL," *Science*, 321 (5889), 686-691 (2008), author manuscript.
Ogretmen et al., "Biologically active sphingolipids in cancer pathogenesis and treatment," *Nat. Rev. Cancer*, 4 (8), 604-616 (2004).
Ohteki et al., "Negative regulation of T cell proliferation and interleukin 2 production by the serine threonine kinase GSK-3," *J. Exp. Med.*, 192 (1), 99-104 (2000).
Pearce et al., "Control of effector CD8+ T cell function by the transcription factor Eomesodermin," *Science*, 302 (5647), 1041-1043 (2003).
Perfetto et al., "Quality assurance for polychromatic flow cytometry," *Nat. Protoc.*, 1 (3), 1522-1530 (2006).
Perfetto et al., "Seventeen-colour flow cytometry: unravelling the immune system," *Nat. Rev. Immunol.*, 4 (8), 648-655 (2004).
Prlic et al., "Multiple choices: regulation of memory CD8 T cell generation and homeostasis by interleukin (IL)-7 and IL-15," *J. Exp. Med.*, 195 (12), F49-F52 (2002).
Pule et al., "Virus-specific T cells engineered to coexpress tumor-specific receptors: persistence and antitumor activity in individuals with neuroblastoma," *Nat. Med.*, 14 (11), 1264-1270 (2008), author manuscript.
Roederer, "Spectral compensation for flow cytometry: visualization artifacts, limitations, and caveats," *Cytometry*, 45 (3), 194-205 (2001).
Rutishauser et al., "Transcriptional repressor Blimp-1 promotes CD8(+) T cell terminal differentiation and represses the acquisition of central memory T cell properties," *Immunity*, 31 (2), 296-308 (2009).
Schmitz et al., "An IL-2-dependent switch between CD95 signaling pathways sensitizes primary human T cells toward CD95-mediated activation-induced cell death," *J. Immunol.*, 171 (6), 2930-2936 (2003).
Surh et al., "Homeostatic T cell proliferation: how far can T cells be activated to self-ligands?," *J. Exp. Med.*, 192 (4), F9-F14 (2000).
Turtle et al., "A distinct subset of self-renewing human memory CD8+ T cells survives cytotoxic chemotherapy," *Immunity*, 31 (5), 834-844 (2009).
Willinger et al., "Molecular signatures distinguish human central memory from effector memory CD8 T cell subsets," *J. Immunol.*, 175 (9). 5895-5903 (2005).
Written Opinion of the International Searching Authority, Application No. PCT/US2012/053947, dated May 3, 2013.
Zhang et al., "Host-reactive CD8+ memory stem cells in graft-versus-host disease," *Nat. Med.*, 11 (12), 1299-1305 (2005).
Zippelius et al., "Thymic selection generates a large T cell pool recognizing a self-peptide in humans," *J. Exp. Med.*, 195 (4), 485-494 (2002).
Havenith et al., "Analysis of stem-cell-like properties of human CD161++IL-18Rα+ memory CD8+ T cells," *International Immunology*, 24(10) 625-636 (2012).
Gattinoni et al., "A human memory T-cell subset with stem cell-like properties Supplementary Information," *Nat. Med.*, 17(10): 1290-1298 (2011).
Turtle et al., "Innate signals overcome acquired TCR signaling pathway regulation and govern the fate of human CD161hi and CD8α+ semi-invariant T cells," *Blood*, 118(10): 2752-2762 (2011).

* cited by examiner

US 10,316,289 B2

METHODS OF PRODUCING T MEMORY STEM CELL POPULATIONS

STATEMENT REGARDING FEDERALLY SPONSORED RESEARCH AND DEVELOPMENT

This invention was made with Government support under project number Z01ZIABC010763 by the National Institutes of Health, National Cancer Institute. The Government has certain rights in the invention.

CROSS-REFERENCE TO RELATED APPLICATION

This patent application is a U.S. National Phase of International Patent Application No. PCT/US2012/053947, filed Sep. 6, 2012, which is incorporated by reference in its entirety herein.

BACKGROUND OF THE INVENTION

Adoptive cell therapy (ACT) using tumor reactive T cells can produce positive clinical responses in cancer patients. Nevertheless, several obstacles to the successful use of ACT for the treatment of cancer and other diseases remain. For example, T cells isolated from the peripheral blood of a host may not exhibit sufficient tumor-specific reactivity or persist in the peripheral blood upon reinfusion into patients. Accordingly, there is a need for improved methods of obtaining a population of antigen-specific T cells from the peripheral blood of a host that exhibit sufficient tumor-specific reactivity and which persist in the blood of patients.

BRIEF SUMMARY OF THE INVENTION

An embodiment of the invention provides a method of producing an isolated T memory stem cell population, the method comprising (a) isolating naïve T cells from a mammal, wherein the mammal is not a mouse; and (b) activating the naïve T cells and expanding the numbers of naïve T cells in the presence of one or more non-specific T cell stimuli, one or more cytokines, and a glycogen synthase kinase (GSK)-3beta inhibitor.

Another embodiment of the invention provides a method of producing an isolated T memory stem cell population, the method comprising (a) isolating lymphocytes from a mammal; and (b) sorting the lymphocytes using flow cytometry into a population comprising a phenotype comprising (i) CD95+, CD45RO−, and CCR7+; and (ii) CD62L+ or one or more of CD27+, CD28+, CD45RA+, and CD127+ to produce an isolated T memory stem cell population.

Still another embodiment of the invention provides a method of producing an isolated T memory stem cell population, the method comprising (a) isolating lymphocytes from a mammal; and (b) sorting the lymphocytes using flow cytometry into a population comprising a phenotype comprising (i) CD95+ and/or CXCR3+; and (ii) CD45RA+, CCR7+, and CD28+ to produce an isolated T memory stem cell population.

Another embodiment of the invention provides an isolated or purified T memory stem cell comprising a phenotype comprising: (a) CD95+, CD45RO−, and CCR7+; and (b) CD62L+ or one or more of CD27+, CD28+, CD45RA+, and CD127+.

Yet another embodiment of the invention provides an isolated or purified T memory stem cell comprising a phenotype comprising (a) CD95+ and/or CXCR3+; and (b) CD45RA+, CCR7+, and CD28+.

Additional embodiments of the invention provide related populations of cells, pharmaceutical compositions, and methods of treating or preventing cancer.

$SI=2^{PI}P_{RP}$, PI=Proliferation Index, $P_{RP}$=Percent of cells retaining the input phenotype. Graph depicts the results from 4 healthy donors; *p=<0.05.

Figure 8:
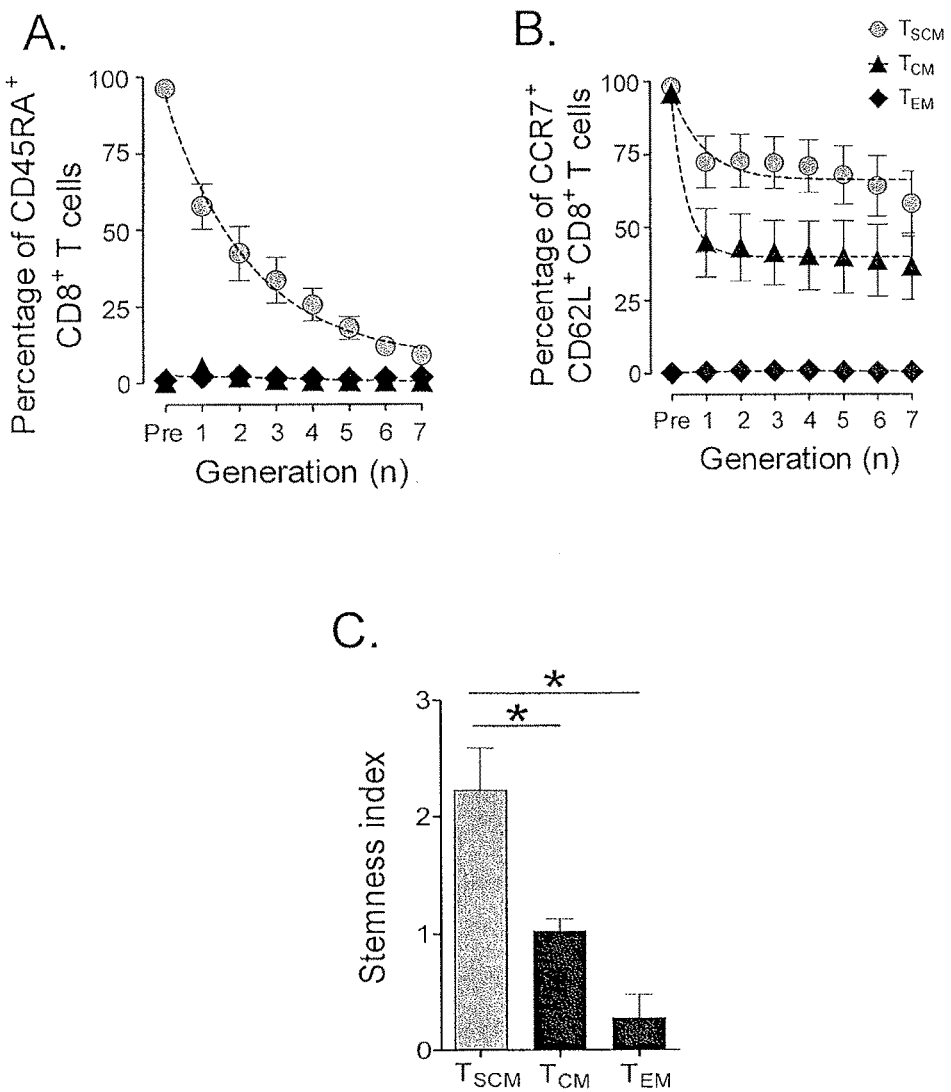

FIGS. 8A and 8B are graphs showing the percentage of $CD8^+$ $T_{SCM}$ (circles) $T_{CM}$ (triangles) or $T_{EM}$ (diamonds) expressing CCR7 and CD62L (8B) and CD45RA (8A) relative to cell division after stimulation with α-CD3/CD2/CD28-coated beads for 6 days. The phenotype of sorted $CD8^+$ T cell subsets before stimulation is indicated as "Pre."

FIG. 8C is a graph showing the stemness index of $CD8^+$ $T_{SCM}$, $T_{CM}$, and $T_{EM}$. Data are represented as means±s.e.m. of 4 donors. *P<0.05 (t test).

Figure 9:
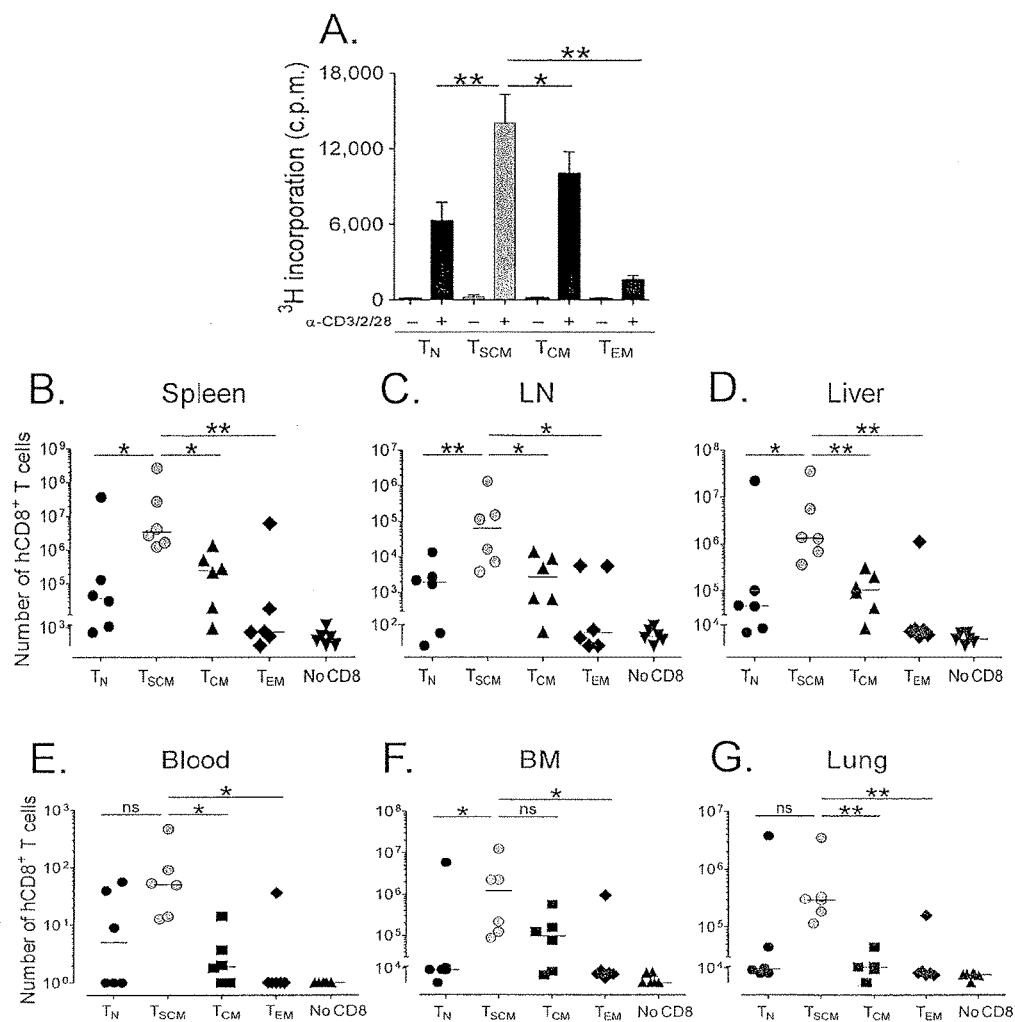

FIG. 9A is a graph showing $^3$H-thymidine incorporation by sorted $CD8^+$ $T_N$, $T_{SCM}$, $T_{CM}$, or $T_{EM}$ after stimulation with α-CD3/CD2/CD28-coated beads. Data are represented as means±s.e.m. of ten donors. Results are normalized to the number of seeded cells, as different cell numbers were obtained from different sorts. c.p.m., counts per min. *P<0.05; P<0.01; *P<0.001 (t test).

FIGS. 9B-9G are graphs showing total human $CD8^+$ T cell recovery in the spleens (9B), lymph node (LN) (9C) livers (9D), blood (9E), bone marrow (9F), or lungs (9G) from six NSG mice 4 weeks after adoptive transfer of $CD4^+$ T cells with or without sorted $CD8^+$ $T_N$, $T_{SCM}$, $T_{CM}$, or $T_{EM}$. A total of six mice per T cell subset from two independent experiments (three replicate mice per T cell subset per experiment) are shown. Horizontal bars indicate median values. *P<0.05; **P<0.01 (t test).

Figure 10:
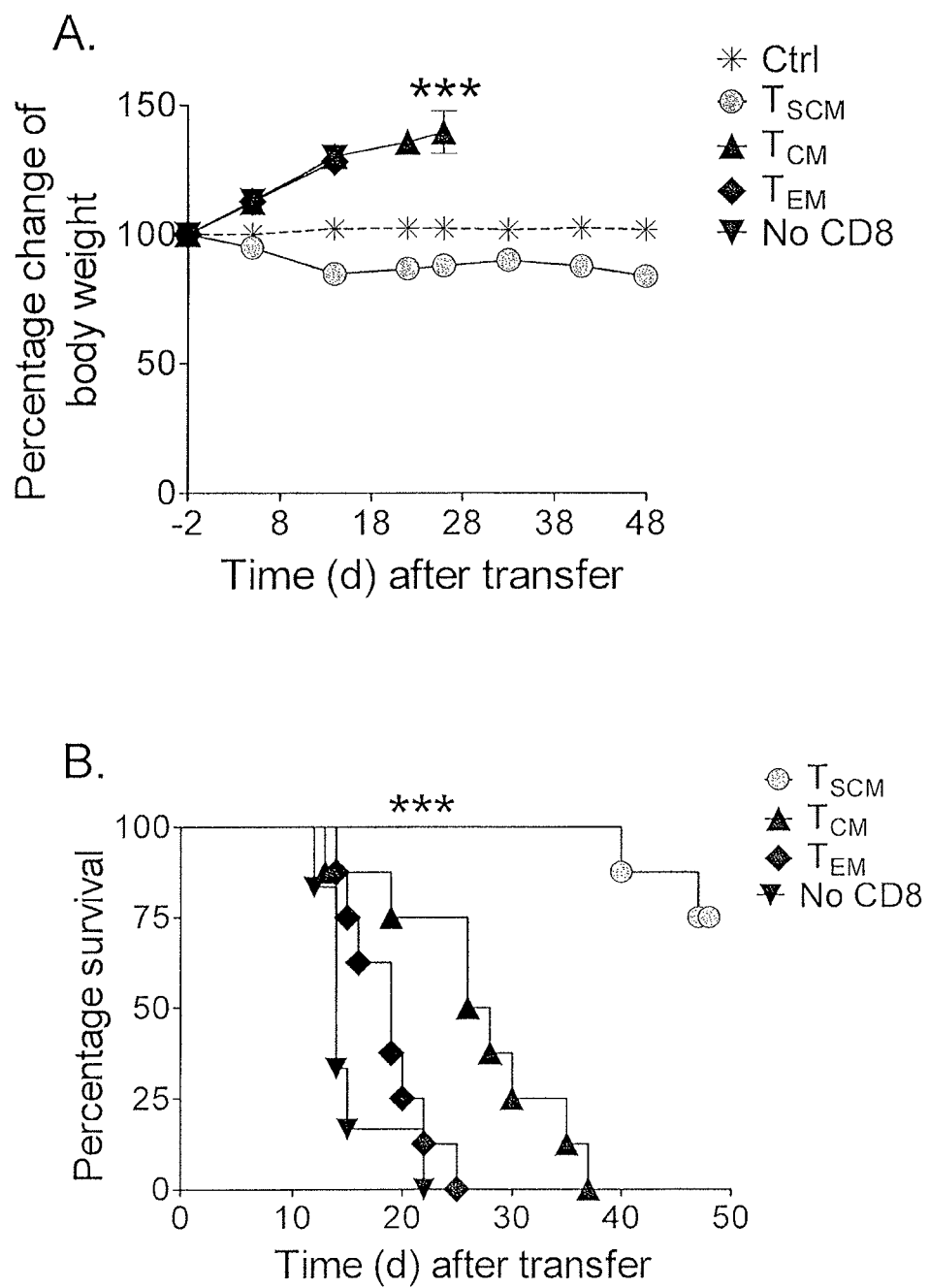

FIGS. 10A and 10B are graphs showing percentage change of body weight (10A) or survival (10B) of untreated (*) mice or NSG mice bearing M108-luciferase mesothelioma after adoptive transfer of $CD4^+$ T cells ($10^6$) with or without (▼) sorted $CD8^+$ $T_{SCM}$ (circles), $T_{CM}$ (▲), or $T_{EM}$ (diamonds) (3×$10^6$) expressing a mesothelin-specific chimeric antigen receptor. ***P<0.001, one-way repeated measures ANOVA (e) and log-rank (Mantel-Cox) test (f).

FIGS. 11A-11D are graphs showing the gating strategy for the identification of human and rhesus $T_{SCM}$ cells. Human and NHP PBMC are stained as indicated in Table 1, Panel #1 and Panel #3, respectively. Both panels include anti-CD4 conjugated to Qdot 585 in addition to anti-CD8 conjugated to Pacific Blue, to allow the simultaneous identification of CD4+ and CD8+ T cells (11D). These T cells are identified by first gating on singlets (FSC-H vs. FSC-A) (11A), live CD3+ T cells (CD3 vs. Dump/AQUA) (11B) and lymphocytes (SSC vs. FSC) (11C).

FIGS. 11E-11L are graphs showing human cells sorted for CCR7 and CD45RO expression (CD8+ in 11E and CD4+ in 11I); CD62L and SSC expression (CD8+ in 11F and CD4+ in 11J); CD95 and CCR7 expression (CD8+ in 11G and CD4+ 11K); and CD95 and CCR7 expression gated on T cells (CD8+ in 11H and CD4+ 11L).

FIGS. 11M-11V are graphs showing rhesus cells sorted for CCR7 and CD45RA expression (CD8+ in 11M and CD4+ in 11R); CD28 and CD95 expression (CD8+ in 11N and CD4+ in 11S); CD95 and CXCR3 expression (CD8+ in 11O and CD4+ 11T); CD95 and CCR7 expression (CD8+ in 11P and CD4+ in 11U); and CD95 and CCR7 expression gated on T cells (CD8+ in 11Q and CD4+ 11V). In NHP CD8+ T cells, CXCR3 is co-expressed with CD95 and thus helps to identify CD8+ $T_{SCM}$ cells, but not CD4+ $T_{SCM}$ cells, as not all CD95+ $T_{SCM}$ in naïve-like CD4+ cells express CXCR3+ (arrow; 11T).

FIGS. 11W-11Z are graphs showing the CD95 FMO control in human CD4+ cells sorted for CD95FMO and CCR7 expression (11W); CD4+ cells sorted for CD95Cy5PE and CCR7 expression (11X); CD8+ cells sorted for CD95FMO and CCR7 expression (11Y); and CD95Cy5PE and CCR7 expression. Dashed bar indicates the threshold for positivity for CD95 expression while the diagonal bar indicates the $T_{SCM}$ gate.

Figure 12:
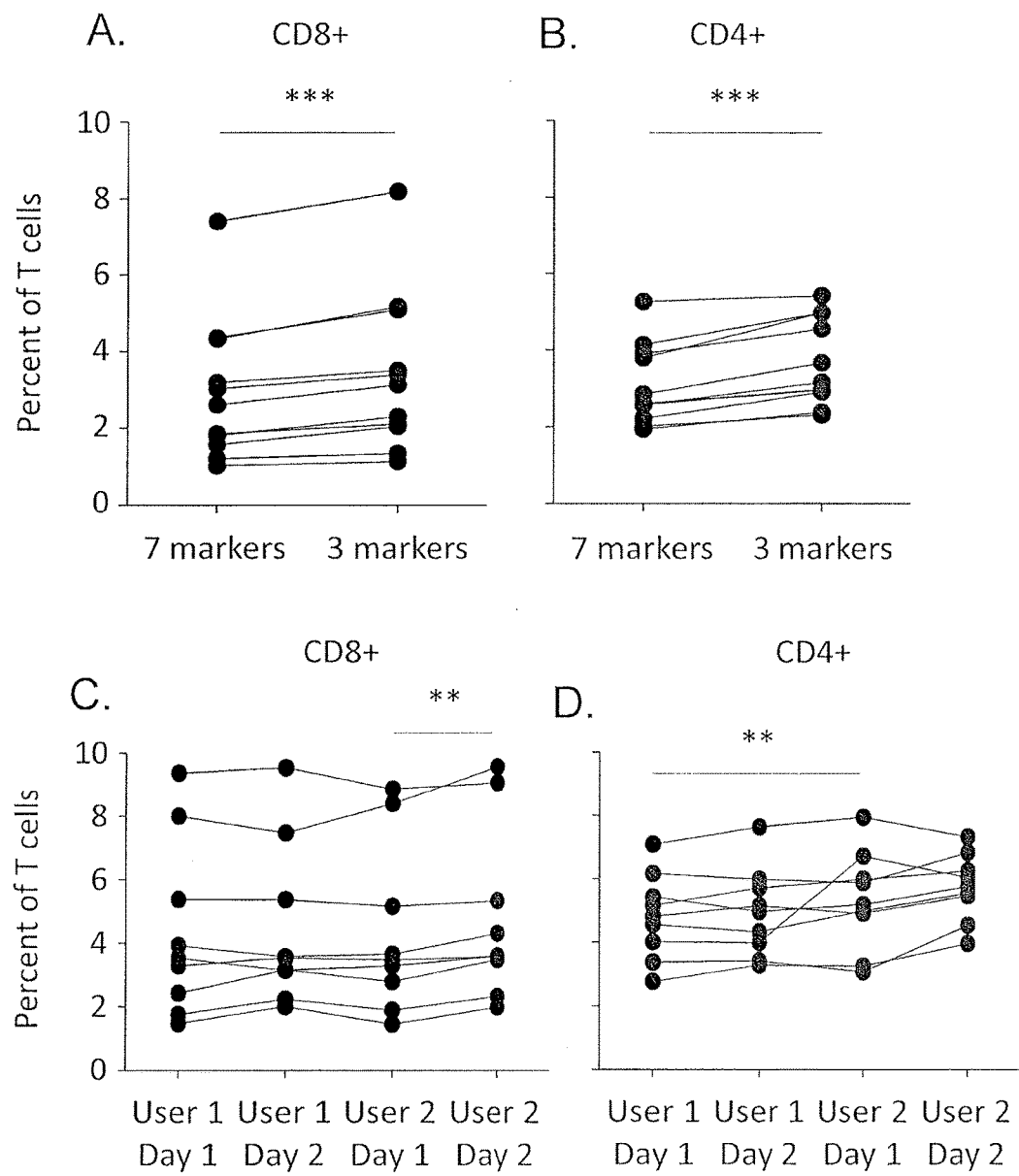
Figure 13:
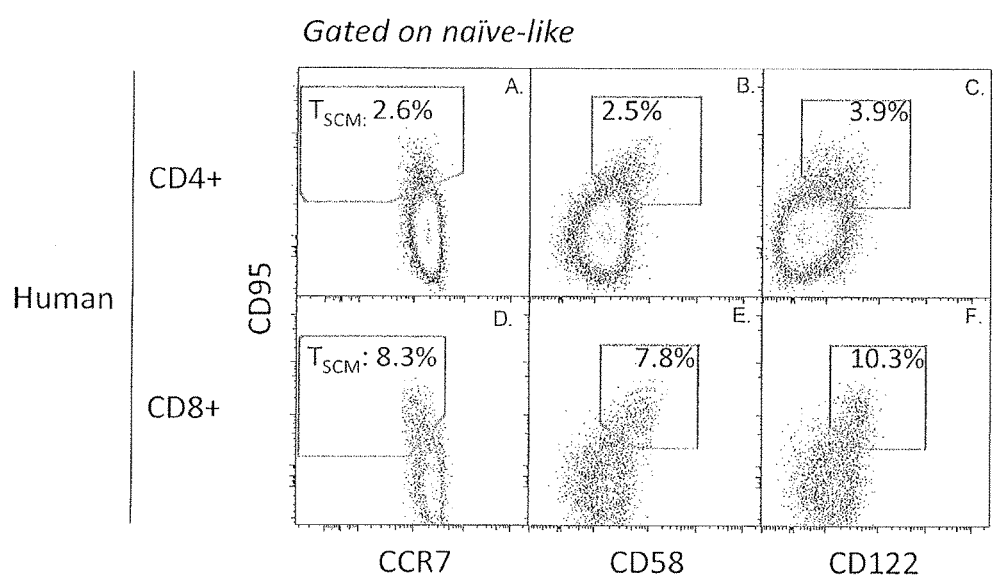
Figure 14:
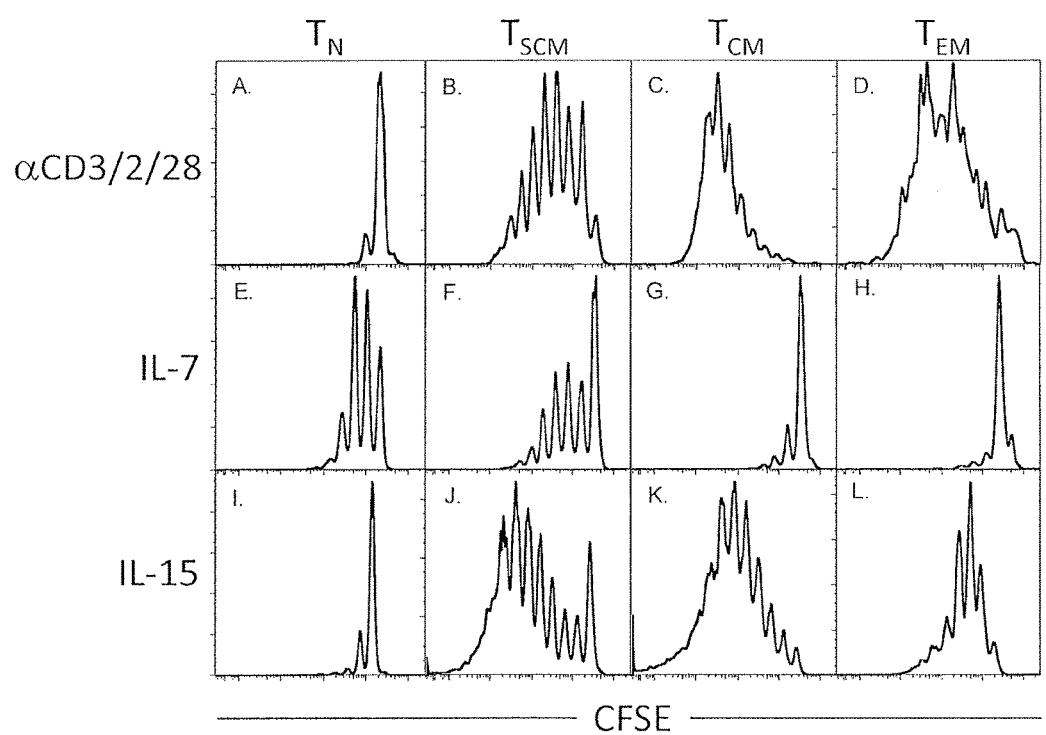

FIGS. 12A-12B are graphs showing the percentage (n=11) of $CD8^+$ or $CD4^+$ naïve-like T cells identified on the basis of CD45RO− CCR7+ CD45RA+ CD62L+ CD27+ CD11adim CD127 (7 markers) or CD45RO− CCR7+ CD62L+ (3 markers). $T_{SCM}$ were subsequently identified as CD95+.

FIGS. 12C-12D are graphs showing the percentage of $CD8^+$ or $CD4^+$ cells identified as $T_{SCM}$ cells by multiple users on multiple days. Data were analyzed by the same user to minimize subjectivity in the gating procedure : P<0.01; *: P<0.001.

Figure 11:
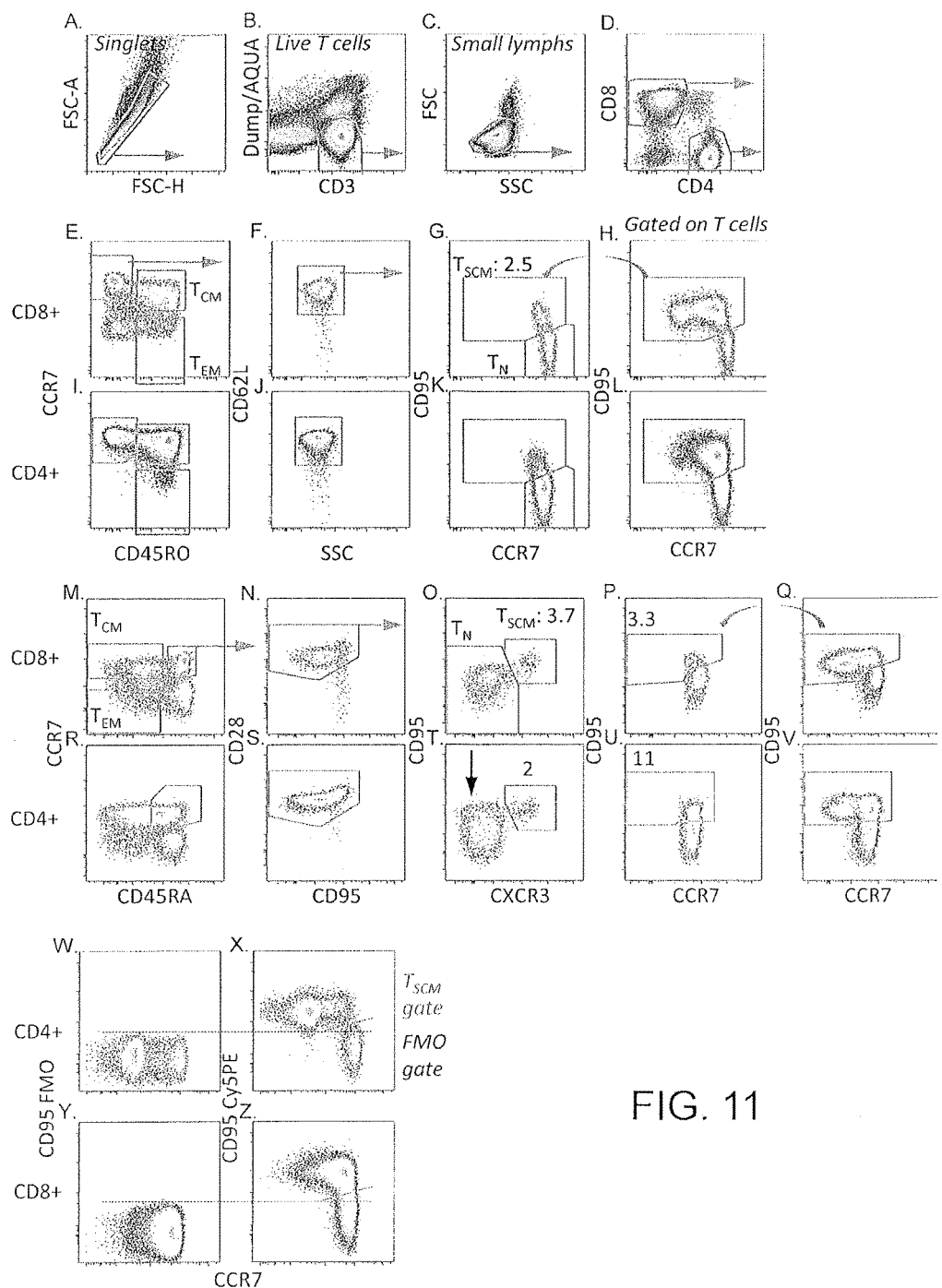

FIGS. 13A-13F are graphs showing the expression of CCR7 (13A and 13D), CD58 (13B and 13E) or CD122 (13C and 13F) vs. CD95 in human CD4+ (13A-13C) and CD8+ (13D-13F) T cells is shown as measured by flow cytometry. The gate identifies $T_{SCM}$ cells as depicted in FIGS. 11E-11V. Numbers indicate the percentage of $T_{SCM}$ cells identified by the gates.

FIGS. 14A-14L are graphs showing the differential response of TN (14A, 14E, and 14I), $T_{SCM}$ (14B, 14F, and 14J), $T_{CM}$ (14C, 14G, and 14K) and TEM (14D, 14H, 14L) (sorted as described in FIGS. 11A-11Z and stained with CFSE), to the stimuli anti αCD3/CD2/CD28 antibody-coated beads for 6 days (14A-14D), 25 ng/mL IL-7 for 14 days (14E-14H) or 25 ng/mL IL-15 for 10 days (14I-14L).

DETAILED DESCRIPTION OF THE INVENTION

An isolated population of memory T cells with enhanced stem cell-like qualities compared with the qualities of central memory T ($T_{CM}$) cells has been discovered. These memory T cells, which are referred to herein as "memory stem T cells" ($T_{SCM}$ cells), advantageously provide an enhanced capacity for self-renewal and multipotency, and are also capable of repopulating differentiated effector lymphocytes in response to antigenic stimuli. It has been discovered that $T_{SCM}$ cells can be effectively generated in vitro using inhibitors of glycogen synthase kinase-3β (GSK-3β). Without being bound by a particular theory or mechanism, it is believed that GSK-3β inhibitors trigger Wnt signaling, which delays or prevents T cell differentiation.

In this regard, the invention provides a method of producing an isolated T memory stem cell population, the method comprising (a) isolating naïve T cells from a mammal, wherein the mammal is not a mouse; and (b) activating the naïve T cells and expanding the numbers of naïve T cells in the presence of one or more non-specific T cell stimuli, one or more cytokines, and a GSK-3beta inhibitor.

The method may comprise isolating naïve T cells from a mammal by any suitable method known in the art. For example, the naïve T cells can be obtained from the mammal by a blood draw or a leukapheresis.

Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). It is preferred that the mammals are non-human primates, e.g., of the order Primates, Ceboids, or Simoids (monkeys) or of the order Anthropoids (humans and apes). In some embodiments, the mammal may be a mammal of the order Rodentia, such as mice and hamsters. In other embodiments, the mammal is not a mouse. Preferably, the mammal is a non-human primate or a human. An especially preferred mammal is the human.

The method comprises activating the naïve T cells and expanding the numbers of naïve T cells by any suitable method known in the art. In an embodiment of the invention, the T cells are activated and the numbers of T cells are expanded in the presence of one or more non-specific T cell stimuli and/or one or more cytokines. In an embodiment of the invention, the T cells are activated and the numbers of T cells are expanded by physically contacting the T cells with one or more non-specific T cell stimuli and/or one or more cytokines. Any one or more non-specific T cell stimuli may be used in the inventive methods. Exemplary non-specific T cell stimuli include anti-4-1BB antibodies, anti-CD3 antibodies and anti-CD28 antibodies. In preferred embodiment, the non-specific T cell stimulus may be anti-CD3 antibodies and anti-CD28 antibodies conjugated to beads. Any one or more cytokines may be used in the inventive methods. Exemplary cytokines include interleukin (IL)-2, IL-7, IL-21, and IL-15.

The GSK-3beta inhibitor may be any suitable compound or composition that inhibits GSK-3beta. Exemplary GSK-3beta inhibitors include lithium chloride (LiCl), TWS119 (3-[[6-(3-aminophenyl)-7H-pyrrolo[2,3-d]pyrimidin-4-yl]oxy]phenol), BIO (6-bromoindirubin-3'-oxime), and CHIR99021 (6-[2-[[4-(2,4-dichlorophenyl)-5-(5-methyl-1H-imidazol-2-yl)pyrimidin-2-yl]amino]ethylamino]pyridine-3-carbonitrile).

Another embodiment of the method provides a method of producing an isolated T memory stem cell population, the method comprising (a) isolating lymphocytes from a mammal; and (b) sorting the lymphocytes using flow cytometry into a population comprising a phenotype comprising (i) CD95+, CD45RO−, and CCR7+; and (ii) CD62L+ or one or more of CD27+, CD28+, CD45RA+, and CD127+ to produce an isolated T memory stem cell population.

The method may comprise isolating lymphocytes from a mammal as described herein with respect to other aspects of the invention. The lymphocytes may be any lymphocytes. Preferably, the lymphocytes are naïve T cells. Preferably, the mammal is a human.

The method may comprise sorting the cells in any suitable manner. Preferably, the sorting is carried out using flow cytometry. The flow cytometry may be carried out using any suitable method known in the art. The flow cytometry may employ any suitable antibodies and stains. Preferably, the flow cytometry is polychromatic flow cytometry.

The method comprises sorting the cells into a population comprising a T memory stem cell phenotype. The phenotype may comprise (e.g., the simultaneous expression of) any one or more of CD95+, CD45RO−, CCR7+, CD62L+, CD27+, CD28+, CD45RA+, and CD127+. Preferably, the method comprises sorting the lymphocytes into a population comprising a phenotype comprising (e.g., the simultaneous expression of) (i) CD95+, CD45RO−, and CCR7+; and (ii) CD62L+ or one or more of CD27+, CD28+, CD45RA+, and CD127+. Preferably, the method comprises sorting the lymphocytes into a population comprising a phenotype comprising (e.g., the simultaneous expression of) all of CD95+, CD45RO−, CCR7+, CD62L+, CD27+, CD28+, CD45RA+, and CD127+. Preferably, the method further comprises sorting the lymphocytes into a population comprising a phenotype further comprising any one or more of CD58+, CD122+, CD3+, CD4+, CD8+, CD11a$^{dim}$ and CD 11a+.

Preferably, the method produces an isolated human T memory stem cell population.

Another embodiment of the invention provides a method of producing an isolated T memory stem cell population, the method comprising (a) isolating lymphocytes from a mammal; (b) sorting the lymphocytes into a population comprising a phenotype comprising (i) CD95+ and/or CXCR3+; and (ii) CD45RA+, CCR7+, and CD28+ using flow cytometry to produce an isolated T memory stem cell population.

The method may comprise isolating lymphocytes from the mammal as described herein with respect to other aspects of the invention. Preferably, the mammal is any non-human primate. An especially preferred mammal is a rhesus macaque.

The method comprises sorting the cells into a population comprising a T memory stem cell phenotype. The phenotype may comprise (e.g., the simultaneous expression of) any one or more of CD95+, CXCR3+, CD45RA+, CCR7+, and CD28+. Preferably, the method comprises sorting the lymphocytes into a population comprising a phenotype comprising (i) CD95+ and/or CXCR3+; and (ii) CD45RA+, CCR7+, and CD28+. The sorting may be carried out as described herein with respect to other aspects of the invention.

In an embodiment of the invention, the method further comprises expanding the numbers of $T_{SCM}$ in vitro. The numbers of $T_{SCM}$ may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), or most preferably at least about 100-fold. The numbers of $T_{SCM}$ may be expanded using any suitable method known in the art. Exemplary methods of expanding the numbers of cells are described in U.S. Pat. No. 8,034,334 and U.S. patent application Ser. No. 13424,646, each of which is incorporated herein by reference.

In an embodiment of the invention, the method further comprises transducing the isolated $T_{SCM}$ with a nucleotide sequence encoding a chimeric antigen receptor (CAR) or a T cell receptor (TCR) (e.g., an exogenous TCR). The CAR or TCR may have antigenic specificity for a cancer antigen or a viral antigen. Exemplary CARs include those described in International Patent Application Publication No. WO 2011041093 and International Application No. PCT/US 12/29861, each of which is incorporated herein by reference. Exemplary TCRs include those described in U.S. Pat. Nos. 7,820,174; 8,088,379; 8,216,565; U.S. Patent Application Publication No. 20090304657; and International Patent Application Publication Nos. WO 2012040012 and WO 2012054825, each of which is incorporated herein by reference. The cells may be transduced using any suitable method known in the art, for example, as described in Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994.

The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. Exemplary cancer antigens may include any one or more of gp100, MART-1, MAGE-A1, MAGE-A2, MAGE-A3, MAGE-A4, MAGE-A5, MAGE-A6, MAGE-A7, MAGE-A8, MAGE-A9, MAGE-A1 0, MAGE-A11, MAGE-A12, NY-ESO-1, vascular endothelial growth factor receptor-2 (VEGFR-2), HER-2, mesothelin, and epidermal growth factor receptor variant III (EGFR III).

The term "viral antigen" as used herein refers to any molecule (e.g., protein, peptide, lipid, carbohydrate, etc.) solely or predominantly expressed by a virus, such that the antigen is associated with the virus. The viral antigen can be an antigen expressed by any virus, including the viruses described herein. The viral antigen may be a viral antigen of only one type of virus, such that the viral antigen is associated with or characteristic of only one type of virus. Alternatively, the viral antigen may be a viral antigen (e.g., may be characteristic) of more than one type of virus. For example, the viral antigen may be expressed by a virus selected from the group consisting of herpes viruses, pox viruses, hepadnaviruses, papilloma viruses, adenoviruses, coronaviruses, orthomyxoviruses, paramyxoviruses, flaviviruses, and caliciviruses.

The inventive methods advantageously isolate $T_{SCM}$ cells. In an embodiment, the $T_{SCM}$ is a human $T_{SCM}$. In an embodiment, the $T_{SCM}$ simultaneously express multiple naïve markers including any one or more of CD45RA, CCR7, CD62L, CD27, CD28, CD127 (IL-7Rα) and CD11a$^{dim}$, while lacking the expression CD45RO. Unlike naïve ($T_N$) cells, $T_{SCM}$ cells also express the memory antigen CD95. In this regard, an embodiment of the invention provides an isolated or purified $T_{SCM}$ comprising a phenotype comprising (e.g., the simultaneous expression of) any one or more of CD95+, CD45RO−, CCR7+, CD62L+, CD27+, CD28+, CD45RA+, and CD127+. Preferably, the $T_{SCM}$ comprises a phenotype comprising (e.g., the simultaneous expression of) (i) CD95+, CD45RO−, and CCR7+; and (ii) CD62L+ or one or more of CD27+, CD28+, CD45RA+, and CD127+. Preferably, the $T_{SCM}$ comprises a phenotype comprising (e.g., the simultaneous expression of) all of CD95+, CD45RO−, CCR7+, CD62L+, CD27+, CD28+, CD45RA+, and CD127+. Preferably, the $T_{SCM}$ comprises a phenotype further comprising any one or more of CD58+, CD122+, CD3+, CD4+, CD8+, CD11a$^{dim}$ and CD11a+.

In an embodiment, the invention also provides an isolated non-human primate (NHP) $T_{SCM}$. The $T_{SCM}$ may comprise a phenotype comprising (e.g., the simultaneous expression of) any one or more of CD95+, CXCR3+, CD45RA+, CCR7+, and CD28+. Preferably, the $T_{SCM}$ comprises a phenotype comprising (i) CD95+ and/or CXCR3+; and (ii) CD45RA+, CCR7+, and CD28+.

In an embodiment of the invention, the $T_{SCM}$ comprises a CAR and/or a TCR (e.g., an exogenous TCR). The CAR and TCR may be as described herein with respect to other aspects of the invention.

The invention further provides an isolated or purified population of cells comprising two or more of any of the isolated $T_{SCM}$ cells described herein.

The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, 90% or can be 100%.

The inventive $T_{SCM}$ cells can be included in a composition, such as a pharmaceutical composition. In this regard, the invention provides a pharmaceutical composition comprising any of the $T_{SCM}$ cells described herein and a phaimaceutically acceptable carrier.

Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use.

The $T_{SCM}$ cells may be administered in any suitable manner. Preferably, the $T_{SCM}$ cells are administered by injection, e.g., intravenously. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the dose, e.g., number of the inventive $T_{SCM}$, administered should be sufficient to effect, e.g., a therapeutic or prophylactic response, in the subject or animal over a reasonable time frame. For example, the number of the inventive $T_{SCM}$ should be sufficient to bind to a cancer antigen, or detect, treat or prevent cancer in a period of from about 2 hours or longer, e.g., 12 to 24 or more hours, from the time of administration. In certain embodiments, the time period could be even longer. The number of the inventive $T_{SCM}$ will be determined by, e.g., the efficacy of the particular inventive $T_{SCM}$ and the condition of the animal (e.g., human), as well as the body weight of the animal (e.g., human) to be treated.

Many assays for determining an administered number of the inventive $T_{SCM}$ are known in the art. For purposes of the invention, an assay, which comprises comparing the extent to which target cells are lysed or one or more cytokines such as, e.g., IFN-γ and IL-2 is secreted upon administration of a given number of such $T_{SCM}$ cells to a mammal among a set of mammals of which is each given a different number of the $T_{SCM}$ cells, could be used to determine a starting number to be administered to a mammal. The extent to which target cells are lysed or cytokines such as, e.g., IFN-γ and IL-2 are secreted upon administration of a certain number can be assayed by methods known in the art. Secretion of cytokines such as, e.g., IL-2, may also provide an indication of the quality (e.g., phenotype and/or effectiveness) of a $T_{SCM}$ cell preparation.

The number of the inventive $T_{SCM}$ also will be determined by the existence, nature and extent of any adverse side effects that might accompany the administration of a particular inventive $T_{SCM}$. Typically, the attending physician will decide the number of the inventive $T_{SCM}$ with which to treat each individual patient, taking into consideration a variety of factors, such as age, body weight, general health, diet, sex, route of administration, and the severity of the condition being treated. By way of example and not intending to limit the invention, the number of the inventive $T_{SCM}$ can be about $10 \times 10^6$ to about $10 \times 10^{11}$ cells per infusion, about $10 \times 10^9$ cells to about $10 \times 10^{11}$ cells per infusion, or $10 \times 10^7$ to about $10 \times 10^9$ cells per infusion. The inventive $T_{SCM}$ may, advantageously, make it possible to effectively treat or prevent cancer by administering about 100 to about 10,000-fold lower numbers of cells as compared to adoptive immunotherapy protocols that do not administer $T_{SCM}$.

It is contemplated that the inventive $T_{SCM}$ cells can be used in methods of treating or preventing cancer. In this regard, the invention provides a method of treating or preventing cancer in a mammal, comprising administering to the mammal any of the pharmaceutical compositions, $T_{SCM}$ cells, or populations of $T_{SCM}$ cells described herein in an amount effective to treat or prevent cancer in the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

For purposes of the inventive methods, wherein $T_{SCM}$ cells or populations of $T_{SCM}$ cells are administered, the cells can be cells that are allogeneic or autologous to the host. Preferably, the cells are autologous to the host.

With respect to the inventive methods, the cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, cervical cancer, gastrointestinal carcinoid tumor, hypopharynx cancer, larynx cancer, liver cancer, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer.

The following examples further illustrate the invention but, of course, should not be construed as in any way limiting its scope.

EXAMPLE 1

This example demonstrates the identification of human T memory stem cells.

Candidate human $T_{SCM}$ cells were generated by activating CD45RO$^-$CD62L$^+$ naïve CD8$^+$ T cells in the presence of the GSK-3β inhibitor TWS119. After 2 weeks, the majority of T cells cultured with TWS119 retained a CD45RO$^-$CD62L$^+$ naïve-like phenotype, whereas in the absence of GSK-3β inhibition, T cells uniformly upregulated the memory marker CD45RO. To determine whether the CD45RO$^-$CD62L$^+$ T cells generated in the presence of TWS119 were truly naïve cells or had acquired memory traits, phenotypic analysis was performed using established markers of T cell activation and differentiation (Appay et al., *Cytometry A* 73: 975-983 (2008)). The vast majority of molecules (CD45RA, CCR7, CD27, IL-2Rα, IL-7Rα, CD69, 41BB, CCR5 and CD57) showed a similar expression pattern between $T_N$ cells and TWS 119-generated naïve-like T cells. However, the naïve-like T cells expressed levels of CD95 and IL-2Rβ similar to those observed in memory T cells. Thus, it was hypothesized that the expression of CD95 and IL-2Rβ in otherwise phenotypically naïve T cells could identify human $T_{SCM}$ cells.

Figure 1:
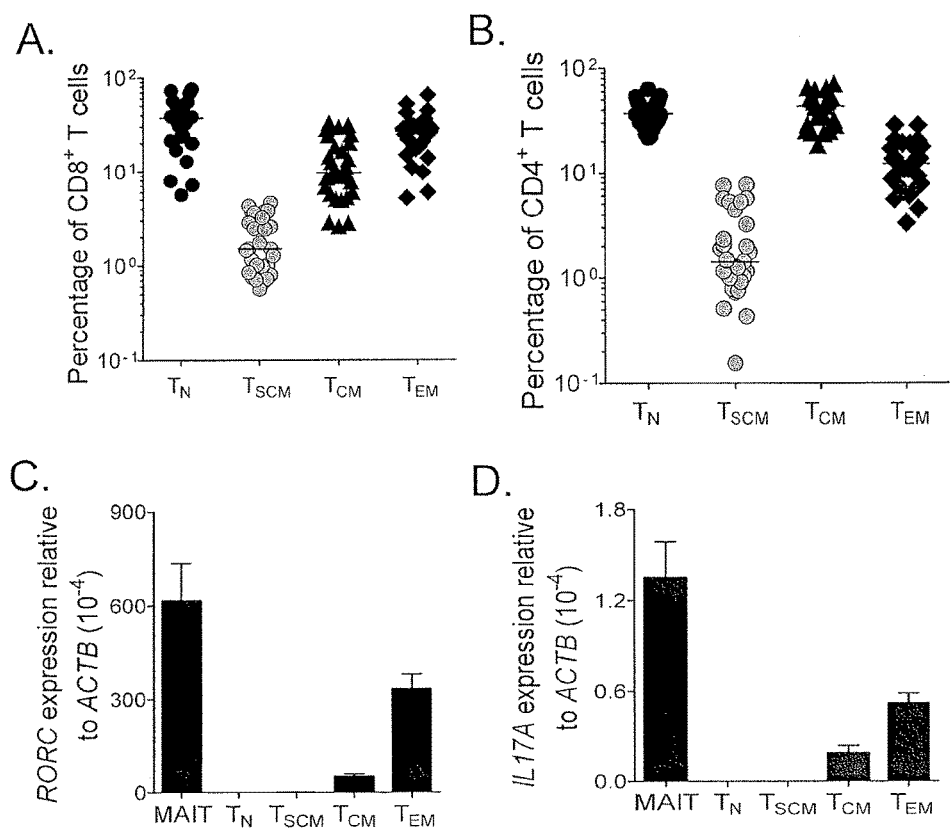
FIGS. 1A and 1B are graphs showing the percentages of circulating CD8$^+$ (1A) and CD4$^+$ (1B) naïve T cells ($T_N$), memory stem cells ($T_{SCM}$), central memory T cells ($T_{CM}$), or effector memory T cells ($T_{EM}$) in 29 healthy donors.
FIGS. 1C and 1D are graphs showing expression of RORC (1C) and IL17A (1D) relative to ACTB by mucosal-associated invariant T (MAIT) cells, $T_N$, $T_{SCM}$, $T_{CM}$, or $T_{EM}$ cells as measured by quantitative reverse-transcriptase polymerase chain reaction (RT-PCR).

To determine if candidate $T_{SCM}$ cells occur naturally, polychromatic flow cytometry (PFC) was used (De Rosa et al., *Nat. Med.*, 7: 245-248 (2001)). Seven markers were used to accurately define $T_N$ cells. Notably, a CD95$^+$IL-2Rβ$^+$ subset was found in CD45RO$^-$CCR7$^+$CD45RA$^+$CD62L$^+$CD27$^+$CD28$^+$IL-7Rα$^+$ naïve-like CD8$^+$ and CD4$^+$ T cells. In 29 healthy donors, these cells, referred to hereafter as $T_{SCM}$ cells, represented about 2-3% of all circulating CD8$^+$ and CD4$^+$ T lymphocytes (FIGS. 1A and 1B). Further phenotypic analysis of T cell differentiation markers revealed that $T_{SCM}$ cells also expressed higher amounts of BCL-2, LFA-1, CXCR3, CXCR4, and lower levels of CD38 and CD31 compared with $T_N$ cells. $T_{SCM}$ cells were phenotypically different from the CD161$^+$, IL-18Rα$^+$ cells described in Turtle et al., *Immunity*, 31: 834-844 (2009) and were not mucosal-associated invariant T cells (MAITs) based on the relative expression of RORC and IL17A (Dusseaux et al., *Blood*, 117: 1250-1259 (2011)) (FIGS. 1C, 1D). Similarly to memory T cells, $T_{SCM}$ cells were detected at low frequencies (<1%) in umbilical cord blood. The phenotype of $T_{SCM}$ cells suggests a tropism for lymphatic tissues.

EXAMPLE 2

This example demonstrates that $T_{SCM}$ cells possess attributes of memory T cells.

Figure 2:
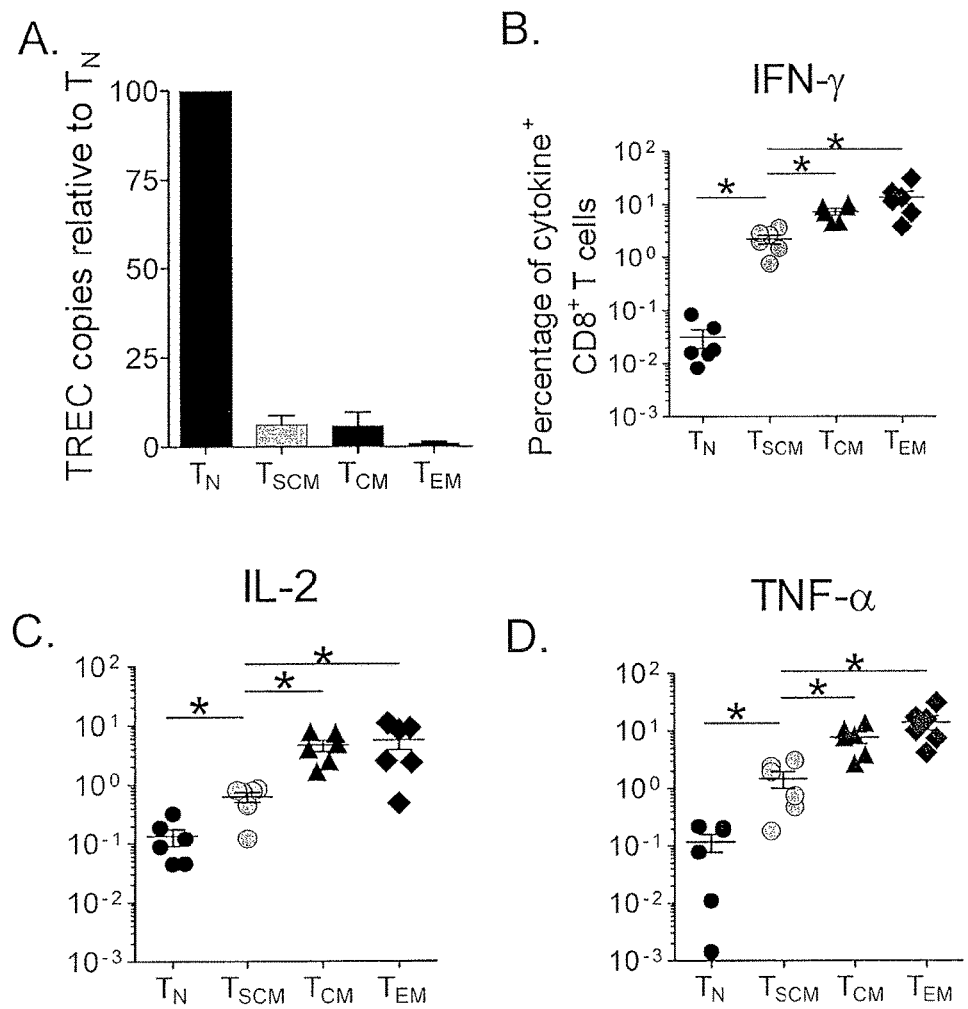
FIG. 2A is a graph showing TREC copy number in sorted CD8$^+$ $T_N$, $T_{SCM}$, $T_{CM}$, or $T_{EM}$ relative to $T_N$ cells. Data are represented as means±standard error of the mean (s.e.m.) of four donors.
FIGS. 2B-2D are graphs showing the percentages of CD8$^+$ $T_N$, $T_{SCM}$, $T_{CM}$, or $T_{EM}$ (from 6 healthy donors) producing interferon (IFN)-γ (2B), interleukin (IL)-2 (2C) or tumor necrosis factor (TNF)-α (2D) 4 hours after exposure to *Staphylococcus* enterotoxin B.

Because of the concomitant expression of numerous markers of naïve T cells as well as molecules of memory differentiation, it remained unclear whether $T_{SCM}$ cells were functionally naïve or memory T cells. Naïve T cells have a high content of T cell receptor (TCR) rearrangement excision circles (TRECs), which are diluted during clonal proliferation (Douek et al., *Nature*, 396: 690-695 (1998)). Like $T_{CM}$ and $T_{EM}$ cells, it was found that $T_{SCM}$ cells had low content of TRECs, indicating that they had undergone several rounds of division (FIG. 2A).

Figure 3:
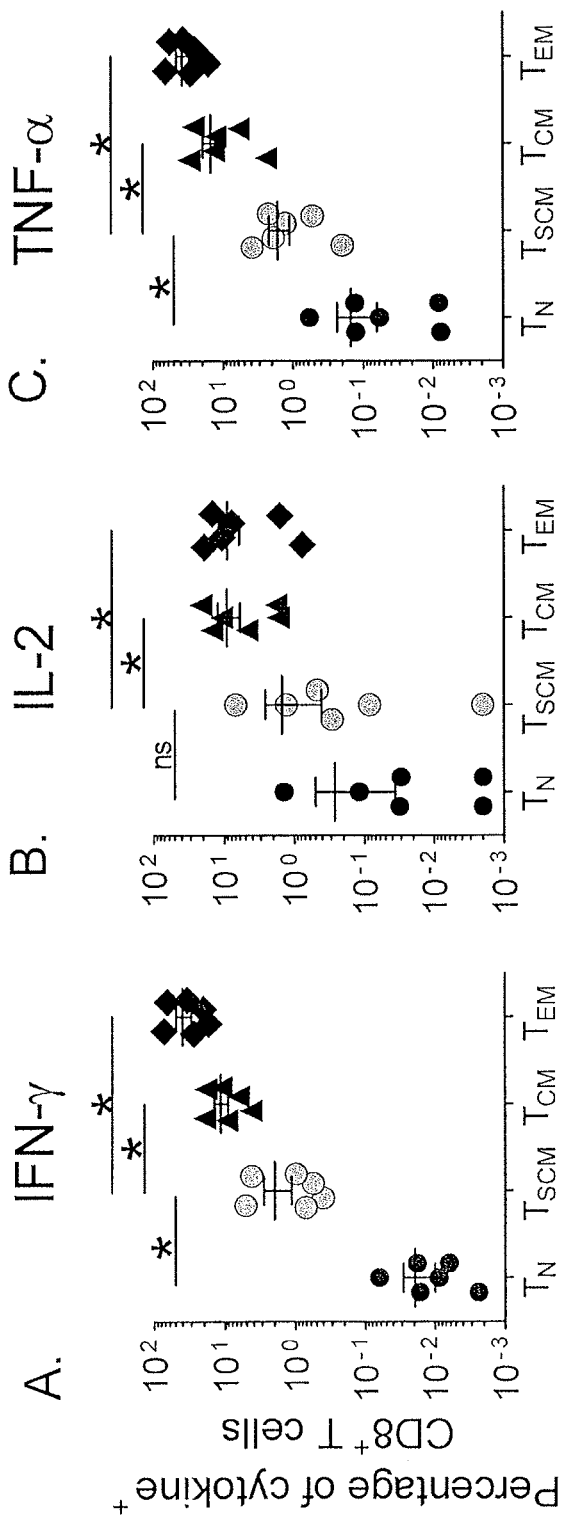
FIGS. 3A-3C are graphs showing the percentages of CD8$^+$ $T_N$, $T_{SCM}$, $T_{CM}$, or $T_{EM}$ (from 6 healthy donors) producing IFN-γ (3A), IL-2 (3B) or TNF-α (3C) 4 hours after stimulation with α-CD3/CD2/CD28 beads.
Figure 4:
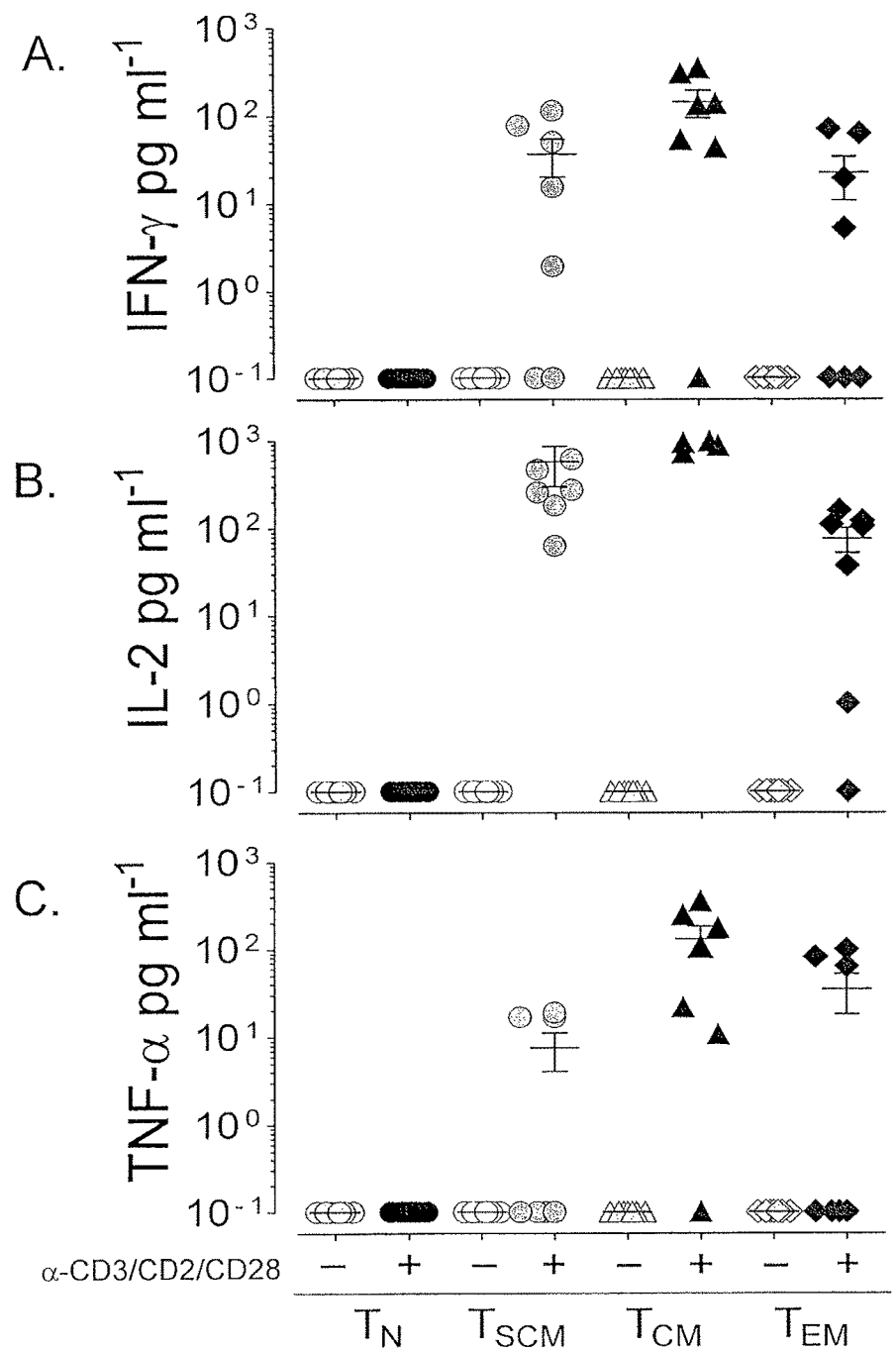
FIGS. 4A-4C are graphs showing IFN-γ (4A), IL-2 (4B) or TNF-α (4C) release by sorted CD8$^+$ $T_N$, $T_{SCM}$, $T_{CM}$, or $T_{EM}$ after 24 hour stimulation with CD3/CD2/CD28 beads.

Memory T cells can also be distinguished from $T_N$ cells by their ability to rapidly acquire effector functions upon antigen rechallenge (Kambayashi et al., *J. Immunol.*, 170: 2399-2408 (2003)). It was found that within 4 hours after exposure to *Staphylococcus* enterotoxin B (SEB), a significant fraction of CD95$^+$ naïve-like CD8$^+$ T cells produced IFN-γ, IL-2 and tumor necrosis factor (TNF)-α, whereas $T_N$ cells remained relatively quiescent (FIGS. 2B, 2C, and 2D). Thus, $T_{SCM}$ cells rapidly acquired effector functions after superantigen stimulation similarly to memory T cells. Notably, the fraction of responding cells, as well as T cell polyfunctionality, progressively increased from $T_N$ cells→$T_{SCM}$ cells→$T_{CM}$ cells→$T_{EM}$ cells (FIGS. 2B, 2C, and 2D), consistent with the hypothesis that $T_{SCM}$ cells are the least differentiated memory subset. Similar findings were observed for CD4$^+$ T cells. The rapid responsiveness of $T_{SCM}$ cells was also observed after polyclonal stimulation with α-CD3/CD2/CD28 beads (FIGS. 3A, 3B, and 3C). Consistent with the intracellular cytokine staining result, it was found that sorted $T_{SCM}$ cells, but not $T_N$ cells, secreted IFN-γ, IL-2 and TNF-α in response to α-CD3/CD2/CD28 stimulation (FIGS. 4A, 4B, and 4C). Thus, $T_{SCM}$ cells possess the memory capability of rapid acquisition of effector functions after TCR stimulation.

Figure 5:
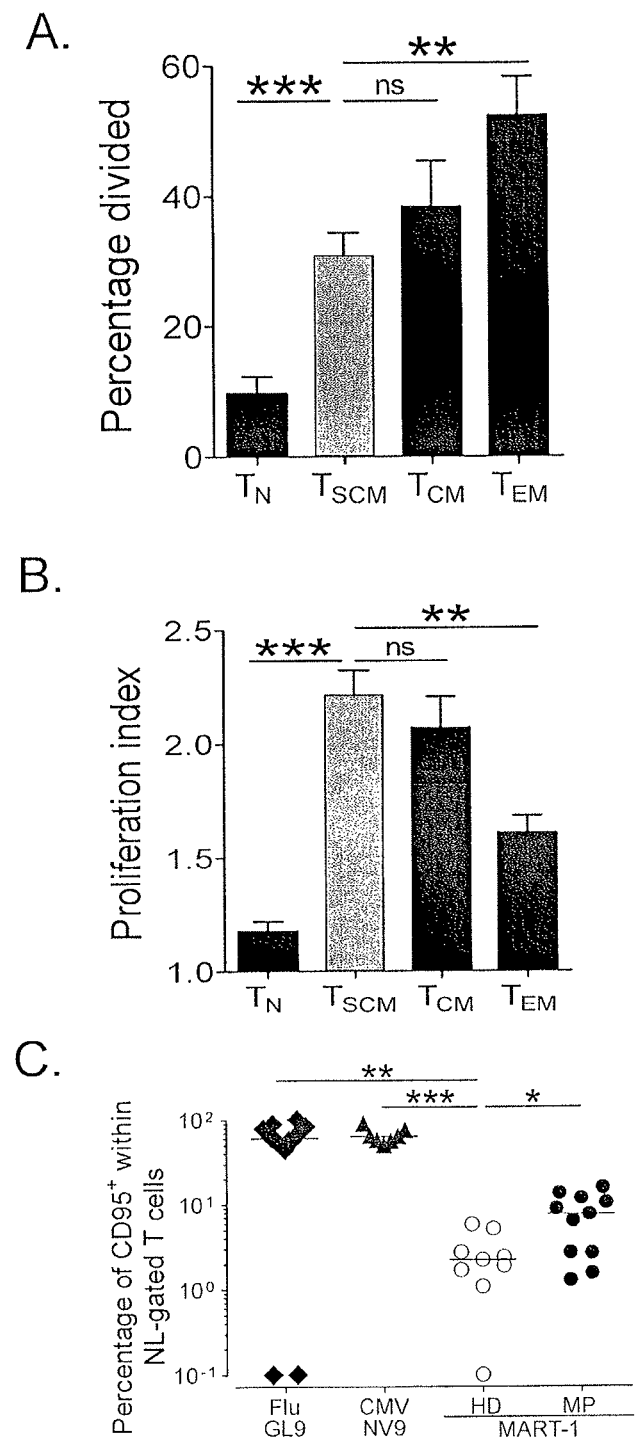
FIGS. 5A and 5B are graphs showing the percentage of divided cells (5A) and proliferation index (5B) of different CD8$^+$ $T_N$, $T_{SCM}$, $T_{CM}$, or $T_{EM}$, after stimulation with 25 ng ml$^{-1}$ of IL-15 for 10 days. Data are represented as means± s.e.m. of 9 donors.
FIG. 5C is a graph showing the percentage of tetramer-binding cells expressing CD95 in the NL (CD45RO$^-$CCR7$^+$ CD45RA$^+$CD27$^+$IL7Rα$^+$) gate, determined by flow cytometry. Data represent the donors tested for tetramer specificity. HD, healthy donor; MP, melanoma patient.
Figure 6:
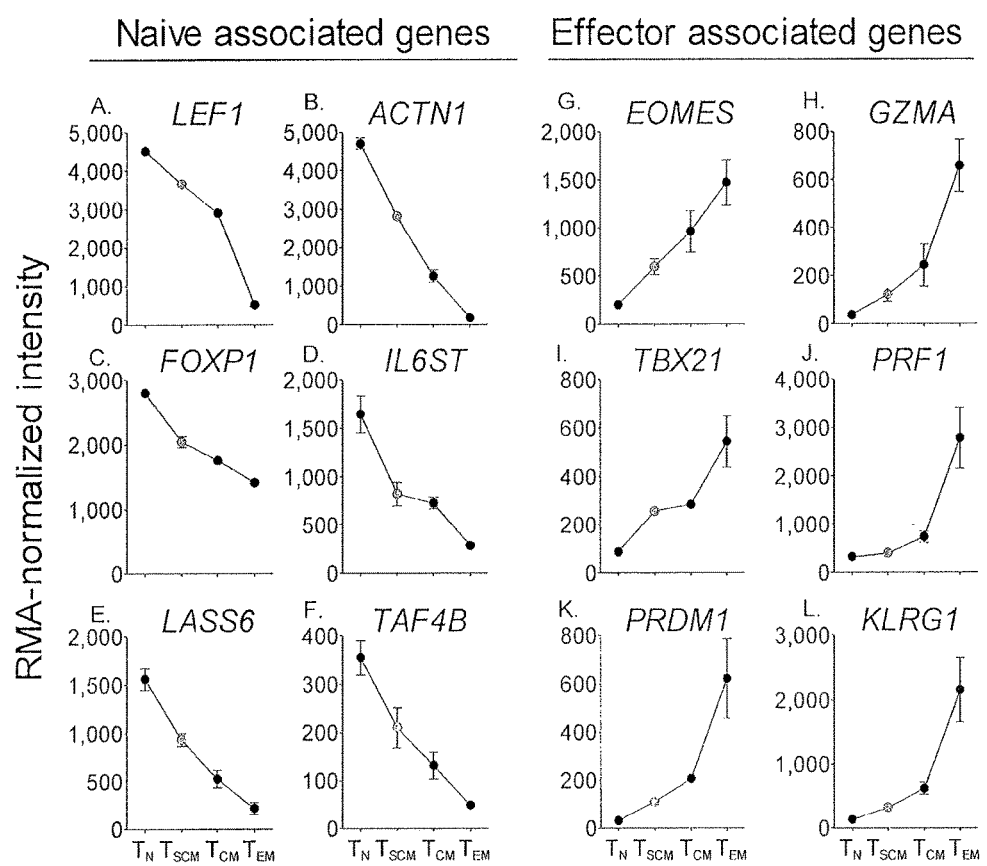
FIGS. 6A-6L are graphs showing the robust multichip analysis (RMA)-normalized intensity of selected genes progressively downregulated (naïve associated genes LEF1 (6A), ACTNI (6B), FOXP1 (6C), IL6ST (6D), LASS6 (6E), or TAF4B (6F)) or upregulated (effector associated genes EOMES (6G), GZMA (6H), TBX21 (6I), PRF1 (6J), PRDM1 (6K), or KLRGI (6L)) from $T_N$ cells, $T_{SCM}$ cells, $T_{CM}$ cells, or $T_{EM}$ cells. Data are represented as means±s.e.m. of three donors.

Unlike $T_N$ cells, memory T cells undergo robust proliferation in the presence of the homeostatic cytokines IL-15 and IL-7 (Surh et al., *J. Exp. Med.*, 192: F9-F14 (2000); Prlic et al., *J. Exp. Med.*, 195: F49-F52 (2002); Lugli et al., *Blood*, 116: 3238-3248 (2010)). It was found that, similarly to CD8$^+$ memory T cells, $T_{SCM}$ cells divided extensively in response to IL-15. Although the majority of $T_{EM}$ cells proliferated (FIG. 5A), they underwent fewer divisions, revealing a lower proliferative potential compared with other memory subsets (FIG. 5B). By contrast, $T_{SCM}$ cells underwent numerous cell divisions (FIG. 5B), although the majority of these cells remained undivided (FIG. 5A). This behavior is reminiscent of stem cells, which are quiescent but can give rise to progeny capable of extensive proliferation and differentiation. Similar findings were observed in the CD4$^+$ T cell compartment in response to IL-7. Thus, $T_{SCM}$ cells have the replicative history and ability to respond rapidly to antigenic and homeostatic stimuli, which are characteristics of memory T cells.

The frequency of naïve CD8$^+$ T cell precursors for a given epitope has been estimated to be between $6\times10^7$ and $5\times10^{-6}$, a range below the limit of peptidemajor histocompatibility complex class I (pMHCI) tetramer detection (Alanio et al., *Blood*, 115: 3718-3725 (2010)). It was reasoned that if tetramer-binding, naïve-like T cells could be measured, they would be enriched in the CD95$^+$ $T_{SCM}$ cell compartment. In donors with detectable naïve-like CD8$^+$ T cells specific to influenza or cytomegalovirus (CMV) epitopes, the vast majority of tetramer-binding cells highly expressed CD95 (FIG. 5C). By contrast, virtually all MART-1 (melanoma antigen recognized by T cells)-specific naïve-like T cells in healthy donors did not express CD95, indicating that these cells were truly naïve (FIG. 5C). Notably, it was found that a significant fraction of MART-1-specific CD8$^+$ T cells had a CD95$^+$ phenotype in 7 out of 11 subjects with metastatic melanoma (FIG. 5C). Thus, tetramer-binding T cells found in the naïve-like T cell compartment could be derived from either increased thymic output (CD95$^-$), as reported for MART-1 in healthy donors (Zippelius et al., *J. Exp. Med.*, 195: 485-494 (2002)), or from antigenic encounter, expansion and differentiation (CD95$^+$). These experiments also revealed that $T_{SCM}$ cells represented a substantial fraction of the corresponding total antigen-specific CD8$^+$ T cell memory responses, averaging 0.6% for CMV pp65495-503, 4.2% for influenza M158-66 and 7.6% for MART-126-35, and that their frequency tended to correlate with that of memory T cells.

To deteline whether $T_{SCM}$ cell clonotypes represent a long-lived population or merely recently activated cells transitioning from a naïve to a memory state, TCR-β sequences of CMV-specific T cell subsets from the same donor spanning a time period of 22 months were analyzed. Similarly to memory T cells, dominant persisting clonotypes in $T_{SCM}$ cells were found, thereby indicating that they represent a stable memory T cell population. These findings show that $T_{SCM}$ cells are long-lived memory T cells with multiple viral and self-tumor specificities.

EXAMPLE 3

This example demonstrates that $T_{SCM}$ cells represent the least differentiated T cell memory subset.

The transcriptome of $T_{SCM}$ cells was compared with naïve and memory T cell subsets and findings were validated with PFC. 900 differentially expressed genes were found among the four CD8$^+$ T cell subsets (P<0.01, false discovery rate<5%). Unsupervised hierarchical clustering revealed that $T_{SCM}$ cells had a distinct gene expression profile more closely related to that of memory T cells than of $T_N$ cells, further corroborating the idea that $T_{SCM}$ cells are a unique T cell memory subset. Consistent with previous findings (Willinger et al., *J. Immunol.*, 175: 5895-5903 (2005)), the expression of the majority of genes (565 of 900) progressively increased (effector-associated genes) or decreased (naïve-associated genes) in the exact order: $T_N$ cells→$T_{SCM}$ cells→$T_{CM}$ cells→$T_{EM}$ cells. Transcripts encoding regulators of effector differentiation and senescence, such as eomesoderminutes (Pearce et al., *Science*, 302: 1041-1043 (2003)), T-box 21 (Joshi et al., *Immunity*, 27: 281-295 (2007)) and PR domain-containing 1 with ZNF domain (Rutishauser et al., *Immunity*, 31: 296-308 (2009)), as well as cytotoxic molecules (for example, granzyme A and perforin) and markers of T cell senescence (for example, killer cell lectin-like receptor subfamily G, member 1, KLRG1) (Joshi et al., *Immunity*, 27: 281-295 (2007)), were increasingly expressed from $T_N$ cells to $T_{EM}$ cells (FIGS. 6A-6L). Conversely, transcripts encoding transcription factors that inhibit T cell activation and differentiation, including lymphoid enhancer-binding factor 1 (Gattinoni et al., *Nat. Med.*, 15: 808-813 (2009)), forkhead box P1 (Feng et al., *Nat. Immunol.*, 12: 544-550 (2011)), and LAG1 homolog, ceramide synthase 6, which promotes cellular quiescence by regulating intracellular ceramide levels (Ogretmen et al., *Nat. Rev. Cancer*, 4: 604-616 (2004)), progressively decreased from $T_N$ cells to $T_{EM}$ cells (FIGS. 6A-6L). These data are consistent with a linear model of T cell differentiation, in which $T_{SCM}$ cells are the least differentiated memory T cell subset.

Multidimensional scaling (MDS) analysis (Khan et al., *Cancer Res.*, 58: 5009-5013 (1998)) confirmed that $T_{SCM}$ cells comprised the memory T cell subset most similar to $T_N$ cells. Indeed, it was found that only 75 genes were differentially expressed between $T_N$ and $T_{SCM}$ cells (P<0.01 and >twofold change in expression) compared with 157 and 226 for $T_{CM}$ and $T_{EM}$ cells, respectively. $T_{SCM}$ and $T_{CM}$ cells were the most closely related T cell subsets, with 20 differentially expressed genes. Among these genes, $T_{SCM}$ cells, like $T_N$ cells, expressed low amounts of HNRPLL (encoding heterogeneous nuclear ribonucleoprotein L-like), a regulator of the alternative splicing of the CD45 pre-mRNA required for efficient CD45RO expression (Oberdoerffer et al., *Science*, 321: 686-691 (2008)), thus confirming the purity of the sorting. When this subset of 20 genes was considered, it was found that $T_{SCM}$ cells had a pattern of expression similar to that of $T_N$ cells, whereas $T_{CM}$ cells clustered with $T_{EM}$ cells, further underscoring the notion that $T_{SCM}$ cells are less differentiated than $T_{CM}$ cells.

EXAMPLE 4

This example demonstrates the enhanced self-renewal and multipotency of $T_{SCM}$ cells.

Figure 7:
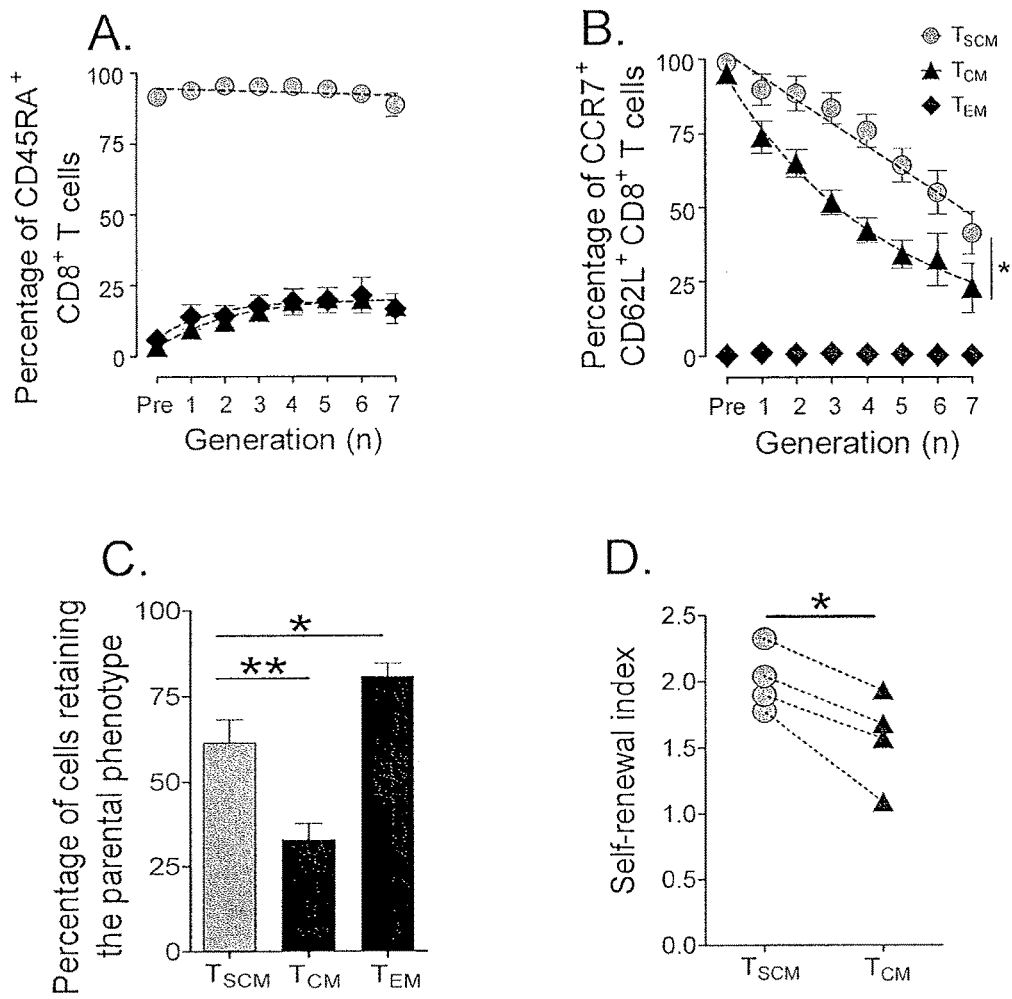
FIGS. 7A and 7B are graphs showing the percentage of CD8$^+$ T cells expressing CCR7 and CD62L (7B) and CD45RA (7A) relative to cell division after exposure to 25 ng ml$^{-1}$ of IL-15 for 10 days. Slopes were compared using a Wilcoxon rank test, *P=0.0391. The phenotype of sorted CD8$^+$ T cell subsets before stimulation is indicated as "Pre."
FIG. 7C is a graph showing the percentage of carboxyfluorescein diacetate succinimidyl ester (CFSE)-diluted CD8$^+$ $T_{SCM}$, $T_{CM}$, or $T_{EM}$ that retained the parental phenotype after stimulation with 25 ng ml$^{-1}$ of IL-15 for 10 days. *P<0.05; **P<0.01 (t test).
FIG. 7D is a graph showing the self-renewal index (SI) of CD8+ memory T cell subsets following secondary stimulation with 25 ng ml$^{-1}$ of IL-15. SI was calculated as follows.

The abilities to self-renew and to differentiate into specialized cell types are qualities of stem cells. To determine whether $T_{SCM}$ have these stem cell-like properties, their capacity to self-renew with homeostatic signals as well as their multipotency after TCR activation were evaluated. After exposure to IL-15, the vast majority of $T_{SCM}$ cells maintained CD45RA$^+$, and retained significantly (P<0.05) higher amounts of CD62L and CCR7 than $T_{CM}$ cells (FIGS. 7A and 7B). At the end of stimulation, about 60% of cells derived from $T_{SCM}$ maintained their phenotypic identity (CCR7$^+$CD62L$^+$CD45RA$^+$ CD45RO$^-$), but only 30% of TCM cells retained their input phenotype (CCR7$^+$CD62L$^+$CD45RA$^-$CD45RO$^+$) (FIG. 7C). $T_{SCM}$ cells also showed greater self-renewal capacity compared with $T_{CM}$ cells after a secondary exposure to IL-15 (FIG. 7D).

After α-CD3/CD2/CD28 stimulation, however, $T_{SCM}$ cells gradually upregulated CD45RO over several cell divisions while acutely downregulating CD62L and CCR7 (FIGS. 8A and 8B). These dynamic changes in phenotype resulted in a diverse progeny, comprising about 50% of $T_{CM}$ cells and 4% of $T_{EM}$ cells. Most notably, 15% of $T_{SCM}$-derived cells maintained a CCR7$^+$CD62L$^+$CD45RA$^+$CD45RO$^-$ phenotype even after this potent stimulus, thus indicating that $T_{SCM}$ cells have the multipotent capacity to derive all memory T cell subsets. By contrast, it was found that $T_{CM}$ cells retained a central memory phenotype or differentiated into $T_{EM}$ cells, but they did not generate $T_{SCM}$ cells. Consistent with their advanced differentiation state, $T_{EM}$ cells did not reacquire CD62L or CCR7 and did not dedifferentiate into $T_{CM}$ or $T_{SCM}$ cells after either IL-15 or α-CD3/CD2/CD28 stimulation (FIGS. 7A-7C and 8A-8B). Taken together, these findings suggest that $T_{SCM}$ cells have the stem cell-like properties of self-renewal and multipotency in vitro (FIG. 8C).

EXAMPLE 5

This example demonstrates the increased proliferative capacity, survival and antitumor activity of $T_{SCM}$ cells.

To evaluate the replicative responses of $T_{SCM}$ cells, $^3$H-thymidine incorporation after TCR stimulation was measured. $T_{CM}$ and $T_N$ cells showed increased proliferative responses compared with $T_{EM}$ cells, but they were outpaced by $T_{SCM}$ cells (FIG. 9A). The long-term replicative and survival capacities of $T_{SCM}$ cells was ascertained. CD8$^+$ T cell subsets were adoptively transferred into highly immunodeficient NOD.Cg-Prkde$^{scid}$Il2rg$^{tm1wjl}$/SzJ (NSG) mice and T cell engraftment was evaluated 1 month after transfer. CD8-depleted peripheral blood mononuclear cells (PBMCs) were co-transferred to provide a source of human cytokines and co-stimulatory molecules (Carpenito et al., *Proc. Natl. Acad. Sci. USA*, 106: 3360-3365 (2009)). It was found that $T_{SCM}$ cells engrafted with 10- to 100-fold more progeny than $T_{CM}$ or $T_N$ cells in both lymphoid and non-lymphoid tissues (FIGS. 9B-9G). Notably, $T_{EM}$ cells, which resemble cell populations used in current clinical trials for adoptive immunotherapy (Gattinoni et al., *Nat. Rev. Immunol.*, 6: 383-393 (2006); June et al., *J. Clin. Invest.*, 117: 1466-1476 (2007)), had a poor proliferative and survival capability resulting in negligible engraftment one month after transfer (FIGS. 9B-9G). Although the CD8$^+$ T cell subsets differentiated into effector cells, perhaps as a result of encounter with homeostatic cytokines and with xenogeneic major histocompatibility antigens, the adoptive transfer in NSG mice suggests that $T_{SCM}$ cells have enhanced replicative and survival capabilities compared with naïve and memory subsets.

T cell proliferative and survival capacities correlate with the antitumor efficacy of adoptively transferred T cells (Gattinoni et al., *Nat. Rev. Immunol.*, 6: 383-393 (2006); June et al., *J. Clin. Invest.*, 117: 1466-1476 (2007); Gattinoni et al., *J. Clin. Invest.*, 115: 1616-1626 (2005); Klebanoff et al., *Proc. Natl. Acad. Sci. USA*, 102: 9571-9576 (2005); Hinrichs et al., *Proc. Natl. Acad. Sci. USA*, 106: 17469-17474 (2009)). TCR or chimeric antigen receptor (CAR) gene engineering may be used in the clinic to redirect the specificity of circulating T cells toward the desired target (Morgan et al., *Science*, 314: 126-129 (2006); Pule et al., *Nat. Med.*, 14: 1264-1270 (2008)). This approach was exploited, coupled to the pharmacological activation of Wnt signaling, to generate high numbers of mesothelin-specific ex vivo-generated memory T cell subsets to test in a xenograft tumor model that we recently established (Carpenito et al., *Proc. Natl. Acad. Sci. USA*, 106: 3360-3365 (2009)). Mesothelin-specific $T_{SCM}$, $T_{CM}$ or $T_{EM}$ cells were co-transferred with mesothelin-specific CD4$^+$ T cells into NSG mice bearing luciferase-expressing M108 mesothelioma established for 3 months in the peritoneum. To generate a treatment window, 3×10$^6$ CD8$^+$ T cells and 10$^6$ CD4$^+$ T cells were administered, about 10% of the previously described curative dose in this humanized tumor model (Carpenito et al., *Proc. Natl. Acad. Sci. USA*, 106: 3360-3365 (2009)). $T_{EM}$ cells mediated poor antitumor responses, as indicated by the high intensity of the tumor-derived bioluminescent signal in the abdomen and the ascites-dependent weight gain (FIG. 10A). Furthermore, the transfer of $T_{EM}$ cells did not significantly extend the survival of the mice compared with CD4$^+$ T cells alone (FIG. 10B). $T_{CM}$ cells were more effective than $T_{EM}$ cells but all mice died from tumor progression within 40 days after treatment (FIGS. 10A-10B). In contrast, $T_{SCM}$ cells triggered tumor regression and cure in mice that otherwise died within 2-3 weeks in the absence of CD8$^+$ T cell transfer (FIGS. 10A-10B). The late mortality of mice receiving $T_{SCM}$ cells was ascribed to the development of xenogeneic graft-versus-host disease, as manifested by loss of body weight (FIG. 10A). These data suggest that adoptively transferred $T_{SCM}$ cells have enhanced antitumor activity and are more therapeutically effective than $T_{CM}$ and $T_{EM}$ cells in mice.

EXAMPLE 6

This example demonstrates a method of isolating a memory stem cell population.

Human and non-human primate (NHP) $T_{SCM}$ cells are relatively rare, comprising about 2-4% of total CD4$^+$ or CD8$^+$ T cells in the blood. By polychromatic flow cytometry, human $T_{SCM}$ were characterized as simultaneously expressing multiple naïve markers including CD45RA, CCR7, CD62L, CD27, CD28, CD127 (IL-7Rα) and CD11a$^{dim}$ and lacking CD45RO; unlike naïve ($T_N$) cells, they also express the memory antigen CD95. However, the simultaneous analysis of all of these nine markers is not necessary for the identification of human $T_{SCM}$ cells (FIGS. 12A and 12B). 7- or 8-color panels (Table 1) accurately identify and allow for sorting of human and NHP $T_{SCM}$ using commonly-available flow cytometers. All anti-body/fluorochrome combinations described are commercially available.

TABLE 1

|  | Panel # | | |
| --- | --- | --- | --- |
|  | 1 | 2 | 3 |
| Target cell | Human $T_{SCM}$ (bulk or antigen-specific) | Human $T_{SCM}$ (bulk or antigen-specific) | NHP $T_{SCM}$ |
| Source of cells | Fresh | Cryopreserved | Fresh or Cryopreserved |
| AmCyan | AQUA fluorescent reactive dye | AQUA Live/ Dead fluorescent reactive dye | AQUA Live/ Dead fluorescent reactive dye |
| APC-Cy7 | CD3 | CD3 | CD3 |
| Pacific Blue | CD4 or CD8 | CD4 or CD8 | CD4 or CD8 |
| APC | CD45RO | CD45RO | CD95 |
| FITC | CCR 7 | CCR7 | CCR7 |
| PE-Cy7 | CD62L | CD27 | CD45RA |
| PE-Cy5 | CD95 | CD95 |  |
| ECD | — | — | CD28 |
| PE | MHC class I tetramer CD58 CD122 | MHC class I tetramer CD58 CD122 | CXCR3 |

For human cells (Table 1, panels #1 and #2), the panels include: i) a "dump" channel to exclude dead cells with a viability dye; ii) antibodies to CD3, CD8 and CD4 to define the lineage of interest; iii) antibodies to CD45RO, CCR7 and either CD62L or a different marker expressed by naïve cells (e.g. CD27, CD28 or CD45RA) to identify naïve-like cells and subsets of memory cells (De Rosa et al., Nat. Med., 7: 245-248 (2001)); iv) and anti-CD95 to discriminate CD95$^-$ $T_N$ from CD95$^+$ $T_{SCM}$. These panels leave the PE channel open to accommodate an additional antibody of interest, an MHC class I tetramer for the identification of antigen-specific CD8$^+$ T cells, or anti-CD58 or anti-CD122 (FIGS. 13A-13F). CD58, the lymphocyte function-associated antigen (LFA)-3, belongs to the immunoglobulin superfamily and mediates the interaction of lymphocytes to CD2, expressed on a variety of cell types including the endothelium. CD122 is the β chain of the IL-2IL-15 receptor complex which forms a low affinity receptor together with the γ chain. Both CD58 and CD122 are found at higher levels on memory cells and $T_{SCM}$ cells than on $T_N$. This differential expression is utilized to better identify $T_{SCM}$ cells (FIGS. 13A-13F). Anti-CD95 antibodies are available through multiple vendors and as conjugated to different fluorochromes, thus allowing the design of complex and interchangeable multicolor panels. Staining for CD95 provides a better separation of $T_{SCM}$ cells from $T_N$ by flow cytometry compared to CD58 and CD122. However, the vast majority of CD95$^+$ $T_{SCM}$ cells also co-expresses these markers. $T_{SCM}$ cells identified on the basis of the increased expression of CD58 or CD122 have also increased expression of the $T_{SCM}$ core phenotypic marker CD95, thus indicating that CD58 and CD122 are valid markers for the identification of true $T_{SCM}$ cells.

Anti-CD95 clone DX2 antibody (like other anti-CD95 antibodies) is capable of inducing apoptosis in target cells. Although quiescent lymphocytes are generally resistant to CD95-induced apoptosis (Schmitz et al., J. Immunol. 171: 2930-2936 (2003); Lugli et al., Leuk. Res., 33, 140-150 (2009)), sodium azide (NaN$_3$) is included in the staining buffer and the sample is kept cold during long FACS sorting procedures to minimize cellular metabolism.

When quantifying $T_{SCM}$ cells in patient samples, peripheral blood lymphocytes from a healthy donor are included as a control to help set gates. It is found that T cells from patients with different pathologies or receiving different therapies exhibit substantially altered representation of the subsets making it difficult to judge delineation gates "by eye."

A similar combination of antibodies is used to identify NHP $T_{SCM}$ cells, i.e. CD45RA, CCR7, CD28, CD95 and CXCR3 (Table 1, Panel #3).

If flow cytometry sorting is planned, cell staining is preceded by negative magnetic isolation of the target lineage (CD4+ or CD8+) to shorten the sorting time. Sorted cells are subsequently expanded by stimulating with a combination of IL-7, which preferentially expands $T_N$, $T_{SCM}$ and $T_{CM}$, IL-15, which selectively expands memory cells (Lugli et al., Blood, 116: 3238-48 (2010)), or anti-CD3/CD2/CD28 antibody-coated beads. In contrast to the latter, IL-7 and IL-15 mediated expansion partly maintains the initial phenotype of the population (Geginat et al., J. Exp. Med., 194: 1711-1719 (2001); Geginat et al., Blood, 101: 4260-4266 (2003)) rather than inducing excessive proliferation, acquisition of effector function and in vitro-induced senescence (Gattinoni et al., J. Clin. Invest., 115: 1616-1626 (2005)).

Human $T_{SCM}$ cells are identified as expressing multiple markers of $T_N$ but also CD95, which is preferentially found on the surface of memory cells. It was found that three markers, i.e. CD45RO, CCR7 and CD62L, are sufficient for the identification of $T_N$-like cells (defined as CD45RO– CCR7$^+$ CD62L$^+$) and for the exclusion of memory T cell contaminants of unknown function, as can occur when only two markers are used to identify naïve T cells (De Rosa et al., Nat. Med., 7: 245-248 (2001)). Even though statistically significant differences were found, the proportion of CD8$^+$ and CD4$^+$ $T_{SCM}$ cells changes only minimally when $T_N$-like cells are defined on the basis of 7 (mean±SEM CD8$^+$: 2.95±0.56; CD4$^+$: 2.81±0.38) vs. 3 markers (CD8$^+$: 3.40±0.62; CD4$^+$: 3.59±0.45; FIG. 12A). Without being bound by a particular theory or mechanism, it is believed that these differences may be ascribed, at least in part, to the transition from CD45RA to CD45RO expression not being as complete as for other memory-defining antigens, thus some cells with intermediate expression of CD45RA but negative for CD45RO might be included in the final population. If using a flow cytometer with a limited number of detectors (e.g. 8), the use of anti-CD45RO is preferred instead of anti-CD45RA, as anti-CD45RO allows the exclusion of CD45RO$^+$ CD45RA$^+$ activated cells. However, if more detectors are available, additional inclusion of anti-CD45RA better delineates the human $T_{SCM}$ cells. When cryopreserved cells are used, CD62L staining may not be reliable because expression may be lost with the freeze/thaw procedure (Perfetto et al., Nat. Rev. Immunol., 4: 648-655 (2004)). In this case, a different marker is used for the identification of naïve -like cells, such as, e.g., CD27, CD28 or CD127 (IL-7Rα), as depicted in Table 1 (Panel #2).

A standardized gating strategy is developed (FIGS. 11A-11V). It is noted that $T_{SCM}$ cells (especially in humans) have slightly lower levels of CCR7 compared to $T_N$ cells. This property allows better delineation of $T_N$ and $T_{SCM}$ cells when CCR7 is plotted against CD95 expression and is exploited by positioning the sorting gate on a diagonal alongside the $T_{SCM}$ population (FIGS. 11A-11D). Indeed, clear-cut separation of positive and negative expression of CD95 is visualized when using this approach. The gate identifying CD95+ cells is then copied in the same bivariate plot after gating for multiple naïve markers, i.e. CD45RO, CCR7 and CD62LCD27 for human cells and CD45RA, CCR7 and CD28 for rhesus macaques (FIGS. 11A-11V). Negligible differences are observed between experiments performed by different users and in different days by using the mentioned strategy (FIGS. 12C-12D).

Alternatively, the inclusion of more markers in the panel improves separation of the $T_{SCM}$ population; for example, higher levels of CD58 and CD122 are found on $T_{SCM}$ cells compared to $T_N$ cells (FIGS. 13A-13F). Anti-CD58 or anti-CD122 antibodies are available conjugated to PE and are included in both Panel #1 and Panel #2. More complex panels are developed as described in Mahnke et al., *Clin. Lab. Med.*, 27: 469-485 (2007).

A similar combination of antibodies is used to track $T_{SCM}$ cells in rhesus macaques, based on expression of CD45RA, CCR7, CD28 and CD95. In NHP, CD95 expression in the $T_{SCM}$ vs. $T_N$ populations is not as distinct as in humans (FIGS. 11E-11V). Addition of anti-CXCR3 to the panel improves identification of $T_{SCM}$ cells in CD8+, but not the CD4+ T cells lineage, as all NHP CD8+ but not CD4+ $T_{SCM}$ express CXCR3 (FIGS. 11E-11V). Indeed, CXCR3 replaces CD95 for the identification and isolation of CD8+ $T_{SCM}$ cells in NHP (FIGS. 11E-11V).

Fluorescence Minus One (FMO) controls, i.e., samples stained with all fluorochromes except the one of interest (Perfetto et al., *Nat. Rev. Immunol.*, 4: 648-655 (2004)), may not be fully informative in this particular example, to identify CD95+ cells, as some $T_N$ express low levels of CD95 (FIGS. 11W-11Z). These cells are not included the $T_{SCM}$ cell gate due to the difficulty of clearly separating CD95$^{dull}$ and CD95− $T_N$ cells. Clear-cut separation of CD95 expression is easily visualized by plotting CD95 vs. CCR7, as described above. However, FMO controls are used to guide the gating procedure and to reveal compensation artifacts.

The flow cytometer is setup as described in Perfetto et al., *Nat. Protoc.* 1: 1522-1530 (2006). The flow cytometer setup includes setting detector photomultiplier (PMT) voltages in advance using quality control reagents, such as pre-stained beads, thereby ensuring the greatest signal-to-background separation. Using such procedures, no changes in PMT settings are needed before the initiation of the experiment, thus the time spent at the machine is limited to the acquisition of the sample. Quality control of laser alignment, laser delays and PMT transmission is checked before every experiment by running Rainbow beads, as described (Perfetto et al., *Nat. Protoc.* 1: 1522-1530 (2006)). In order to minimize the time spent at the flow cytometer on the day of the experiment, the experiment template is set up in advance. A rigorous quality assurance/quality control (QAQC) program for instrument alignment and settings facilitates reproducible evaluation of $T_{SCM}$ cells using polychromatic flow cytometry.

The MHC class I tetramer is synthesized and conjugated in the laboratory. All antibodies and tetramers are carefully titrated before use, whether obtained commercially or synthesized in the laboratory. The titre giving the best separation over the background is chosen. However, in some cases, a lower concentration of the antibody is used to minimize "spreading error" to other fluorochromes (i.e., after compensation) (Roederer et al., *Cytometry*, 45: 194-205 (2001)). Detailed theoretical considerations and practical procedures regarding antibody binding to antigen for flow cytometric analyses are carried out as described in Kantor et al., *Handbook of Experimental Immunology*, Vol. 49: 1-13 (Blackwell Science, Herzenberg et al. (1997)).

EXAMPLE 7

This example demonstrates the identification, isolation and in vitro expansion of human $T_{SCM}$ cells.

Reagents

Human peripheral blood or NHP peripheral blood, lymph node or spleen

Ficoll-Paque PLUS (GE Healthcare, Pittsburg, Pa.)

Dulbecco's Phosphate Buffered Saline (DPBS; Life Technologies, Grand Island, N.Y.)

Heat-inactivated Fetal Bovine Serum (HI FBS; Life Technologies)

Penicillin-Streptomycin-Glutamine (Life Technologies)

RPMI 1640 phenol red (Life Technologies)

RPMI 1640 no phenol red (Life Technologies)

HEPES (Life Technologies)

Sodium Azide (NaN$_3$; Sigma-Aldrich)

CD4+ T cell isolation kit II (Miltenyi Biotech, Auburn, Calif.)

CD8+ T cell isolation kit (Miltenyi Biotech)

CD4+ T cell isolation kit, nonhuman primate (Miltenyi Biotech)

CD8+ T cell isolation kit, nonhuman primate (Miltenyi Biotech)

Fluorescently-conjugated anti-human monoclonal antibodies (all listed antibodies are whole immunoglobulin): anti-human CD3 APC-H7 (BD Pharmingen, San Diego, Calif.; clone SK7; IgG$_1$κ), anti-human CD4 Brilliant Violet 421 (Biolegend, San Diego, Calif.; clone OKT4; IgG$_{2b}$ κ); anti-human CD8 Pacific Blue (BD Pharmingen; clone RPA-T8; IgG$_1$κ); anti-human CD45RO APC (BD Pharmingen; clone UCHL1; IgG$_{2a}$κ); anti-human CCR7 FITC (BD Pharmingen; clone 150503; IgG$_{2a}$κ); anti-human CD62L PE-Cy7 (Biolegend; clone DREG-56; IgG$_1$κ); anti-human CD27 PE-Cy7 (Beckman Coulter, Indianapolis, Ind.; clone 1A4CD27; IgG$_1$κ); anti-human CD95 PE-Cy5 (Biolegend; clone DX2; IgG$_1$κ); anti-human CD3 APC-Cy7 (BD Pharmingen; clone SP34-2; IgG$_1$ λ); anti-human CD45RA PE-Cy7 (BD Biosciences; clone L48; IgG$_1$κ); anti-human CD28 ECD (Beckman Coulter; clone CD28.2; IgG$_1$); anti-human CD95 APC (BD Phanningen; clone DX2; IgG$_1$ κ); anti-human CXCR3 PE (BD Pharmingen; clone 1C6/CXCR3; IgG$_1$κ); anti-human CD58 PE (BD Biosciences; clone L306.4; IgG$_{2a}$κ); anti-human CD122 PE (BD Phanningen; clone Mik-β3; IgG$_1$κ). Staining combinations are as described in Table 1. Each lot of antibody is titrated before use MHC Class I tetramers: NIH tetramer core facility Mouse anti-monkey CD3 antibody (Life Technologies; clone FN18; IgG$_1$)

Mouse anti-human CD28 antibody (BD Biosciences; clone CD28.2; IgG$_1$, κ)

LIVE/DEAD AQUA fluorescent reactive dye (Life Technologies)

Each lot of dye is titrated before use.

BD CompBeads anti-mouse Igκ (BD Biosciences)

SPHEROTM COMPtrol goat anti-mouse Ig (WO particles (Spherotech, Lake Forest, Ill.)

R—NH$_2$ Beads (SMPLX Amine active beads; Bangs Laboratories, Fishers, Ind.)

Formaldehyde, 20% aqueous (Tousimis, Rockville, Md.)

Carboxy-Fluorescein di-acetate Succinimidyl Esther (CFSE; Life Technologies)
Recombinant human Interleukin-7 (Peptrotech, Rocky Hill, N.J.)
Recombinant human Interleukin-15 (Peptrotech)
Human T cell activation and expansion kit (Miltenyi Biotech)
Ethidium Bromide (EB; Life Technologies).
Acridine Orange (AO; Life Technologies)
Equipment
5 mL polystyrene round-bottom tubes (BD Falcon, Bedford, Mass.)
15 mL conical tubes (BD Falcon)
50 mL conical tubes (BD Falcon)
1.5 mL Eppendorf tubes (Eppendorf, Hamburg, Germany)
Quadro MACS Starting Kit (Miltenyi Biotec)
Miltenyi LS columns (Miltenyi Biotec)
Flow cytometer or cell sorter equipped with a violet, a blue and a red laser, capable to collect 8 different fluorescences
Tissue culture 6-well plates (Corning, Corning, N.Y.)
Tissue culture 24-well plates (Corning)
Tissue culture 96-well plates (Corning)
Bench-top Ultrasonic Cleaner (Branson, Danbury, Conn.)
Cellometer automated cell counter (Nexcelom Bioscience, Lawrence, Mass.)
Cellometer disposable counting chambers (Nexcelom Bioscience)
Reagent Setup
Complete culture medium (R10): R10 is prepared using 10% (vol/vol) FBS, 1% (vol/vol) Penicillin/Streptomycin/L-Glutamine in RPMI 1640 medium with phenol red.
Staining Buffer I: 4% (vol/vol) FBS in RPMI 1640 medium with no phenol red
Staining Buffer II: 4% (vol/vol) FBS, 0.02% (vol/vol) NaN3 in RPMI 1640 medium with no phenol red
Sorting Buffer: 4% (vol/vol) FBS and 25 mM HEPES in RPMI 1640 medium with no phenol red.
MACS buffer: 5 mL of 0.5 M EDTA stock (5 mM) and 2.5 g BSA is mixed and PBS is added to adjust the volume to 500 mL. The solution is filter-sterilized and degassed.
EB stock solution: 3 mg/mL of EB is mixed in ethanol and stored in dark bottle for 6 months.
AO stock solution: 5 mg/mL of AO is mixed in ethanol and stored in dark bottle for 6 months.
EB/AO working solution: 10 µL of EB stock is added to 10 µL of AO stock and diluted to 1 mL with PBS. (Final concentration (conc.) of EB=30 µg/mL and final conc. AO=50 µg/mL).
AQUA viability dye: AQUA powder is thawed at 37° C. for 30 sec, 50 µL of DMSO is added. The mixture is pipetted thoroughly and stored at −20° C. for up to 3 months.
Bead medium: 2% FBS, 0.02% $NaN_3$ in PBS.
R—$NH_2$ AQUA Compbeads: 1: 5 dilution of the bead stock is made with bead medium (approximately 46.2× $10^6$ beads/mL), 350 µL (16×$10^6$) is taken and washed in PBS, and beads are resuspended in 300 µL of PBS. 100 µL AQUA Dye is added and incubates for 1.5 hours (hr.). Beads are washed 2× with bead medium and resuspended in 2 mL volume. Equal concentration (350 µL) of unstained amine bead is spiked in. Bead media is added to obtain a final volume of 4 mL.
CFSE stock: powder is thawed and resuspended in DMSO at a final concentration of 5 mM.
Anti-monkey CD3 stimulation solution: Antibody is diluted to a final concentration of 10 µg/mL in PBS.
Cell isolation and Staining. Timing: 2 hr for Ficoll separation, 2 hr for magnetic separation, 1.5 hr for fluorescent staining. Lymphocytes are isolated from peripheral blood or from a different site of acquisition by Ficoll gradient centrifugation according to standard techniques. If working with frozen cells, cells are thawed according to standard techniques.

Cell number and viability are determined with CELLOMETER VISION automated cell counter: 20 µL of EBAO working solution is added to 20 µL of cell suspension and counted.

At least 0.5×$10^6$ cells are used for simple phenotyping and 4×$10^6$ cells are used for the analysis of antigen-specific $T_{SCM}$ cells. If sorting is planned, enough cells are started with to obtain the desired number of $T_{SCM}$ cells. The yield after sorting is 1 $T_{SCM}$ cell per 250 peripheral blood mononuclear cells (PBMC) for CD4$^+$ T cells and 1 $T_{SCM}$ cell per 500-1,000 PBMC for CD8$^+$ T cells, depending on the donor. Similar numbers are obtained for NHP $T_{SCM}$ cells. Optionally, if flow cytometry sorting is planned, CD4$^+$ or CD8$^+$ T cell populations are enriched by negative selection with a kit according to the manufacturer's instructions. If performing simple phenotyping or sorting small numbers of $T_{SCM}$ cells, thawing and staining are performed on the same day. If fixed, samples are run the following day. If a considerable number (millions) of $T_{SCM}$ cells are needed, such as for adoptive transfer experiments, flow cytometric sorting may take many hours. Enriched cells are left at 37° C. overnight and surface staining is performed the following day, before sorting. If analyzing mRNA expression by gene array, cells are recovered without interruption and kept at 4° C. to avoid changes in gene expression.

The cells are washed with PBS to remove any residual proteins. The cell suspension is centrifuged for 5 minutes at 400 g at room temperature (RT). An AQUA dye working solution is prepared in excess (15% more than the volume needed for the experiment) by diluting the stock solution in water and vortexing. PBS is added to reach the desired concentration as determined by titration and vortexed. The supernatant is removed from pelleted cells.

AQUA dye working solution is added to the cell pellet, resuspended by pipetting and incubated for 15 minutes at RT in the dark. 100 µL of AQUA dye is used if up to 10×$10^6$ cells are stained. If more cells are used, it is considered that a 100×$10^6$ cell pellet corresponds to a volume of ~100 µL. If 100 µL of staining solution are used to stain such a number of cells, the final concentration of the dye (or of the antibody) is diluted. Therefore, a staining solution is prepared containing 3× or 4× the concentration of the reagent to obtain a final volume of ~200 uL. The staining volume is scaled up accordingly to the number of cells. In any case, the optimal titer of antibodies to be used in sorting experiments is determined by a titration experiment, where for instance 1×, 2×, 4× or 8× the amount of the antibody optimal for staining $10^6$ cells is used. Detailed theoretical considerations and practical procedures regarding antibody binding to antigen for flow cytometric analyses are performed as described in Kantor et al., *Handbook of Experimental Immunology*, 49: 1-13 (Blackwell Science, Herzenberg et al., (1997)).

The cells are washed by adding Staining Buffer I (to dilute staining solution by 20-30 fold). The cells are spun for 5 minutes at 400 g at RT.

CCR7 staining solution is prepared in excess (15% more than the volume needed for the experiment) in FACS buffer I. CCR7 as well as other chemokine receptors recycle through the plasma membrane. $NaN_3$ is not included in the staining buffer as it prevents the internalization of surface antigens and produces a loss of fluorescence intensity. The amount of antibody needed to stain a large number of cells is determined as described above.

Antibody aggregates are removed by spinning the solution in a microfuge at 15,000 g for 5 min. Only the supernatant is collected. The supernatant is removed from the pelleted cells.

CCR7 staining solution is added, the cell pellet is resuspended by pipetting and incubated for 20 minutes at 37° C. in the dark. If using NHP cells, CXCR3 staining is performed at this stage. Incubation at 37° C. allows CCR7 and CXCR3 to recycle through the plasma membrane and improves their detection by producing a gain of fluorescence. However, for rhesus macaques, no difference is seen by staining for CCR7 at 37° C. vs. RT.

The cells are washed with Staining Buffer II and spun for 5 minutes at 400 g at RT. In the meantime, surface staining antibody mix is prepared in excess (15% more than the volume needed for the experiment) and centrifuged at 15,000 g for 5 min. This mix is prepared using Staining Buffer II containing $NaN_3$ to minimize cellular metabolism.

The supernatant is removed from pelleted cells. Mix is added to the cell pellet, resuspended by pipetting and incubated for 20 minutes at RT in the dark. The amount of antibody needed to stain a large number of cells is determined as described above.

Compensation controls are prepared. Beads are vortexed and 30 μL is aliquoted to each tube. A tube is prepared for each fluorochrome plus a tube with beads only (unstained negative control). If using different types of beads or cells for compensation, the relative negative control is included. Compbeads tend to form aggregates over time. Before use, Compbeads are sonicated for 2 min.

The fluorescently-conjugated antibody is added at the same titer that is used for the staining, vortexed and incubated for 15 minutes at RT. The sample and compensation controls are washed with Staining buffer II and spun for 5 minutes at 400 g at RT.

If performing phenotyping, cells are resuspended in 1% PFA solution. If sorting, cells are resuspended in Sorting Buffer. Cells are kept on ice and in the dark. Compensation tube contents are resuspended in the same buffer. If performing a long sort, cells are resuspended in RPMI 1640 medium supplemented with HEPES. Indeed, $CO_2$-based buffers lose pH under high sort pressures, thus reducing cell survival after sort.

Acquisition and cell sorting. Timing: 2-15 h, depending on the number of samples and cells required for the experiment. Compensation controls are run. Compensation matrix is created and applied to tubes, if sorting. Run the samples using the gating strategy shown in FIGS. 11A-11Z.

Using a 70 μm nozzle, the population(s) of interest are sorted: human $T_N$ (CD45RO$^-$CCR7$^+$ CD62L$^+$ CD95$-$); human $T_{SCM}$ (CD45RO$^-$CCR7$^+$ CD62L$^+$ CD95$^+$); human TCM (CD45RO$^+$ CCR7$^+$); human $T_{EM}$ (CD45RO$^+$ CCR7$^-$); NHP $T_N$ (CD45RA$^+$ CCR7$^+$ CD28$^+$ CD95$^-$); NHP $T_{SCM}$ (CD45RA$^+$ CCR7$^+$ CD28$^+$ CD95$^+$); NHP $T_{CM}$ (CD45RA$^-$ CCR7$^+$); NHP $T_{EM}$ (CD45RA$^-$CCR7$^+$). The cells are sorted into a 5 mL Falcon tube or 1.5 mL Eppendorf tube containing R10 complete medium, if cell culture is planned afterwards. 250,000 $T_{SCM}$ cells/h are obtained by flow cytometry sorting. Sorted cells are kept chilled to minimize cellular metabolism. However, the sample is not chilled if a short stimulation is planned, to avoid cell non-responsiveness. The purity of sorted subsets is checked to be >95%.

T cell expansion in vitro. Timing: 7-14 days. If stimulating NHP cells, a plate is coated with anti-monkey CD3 overnight at 4° C. as described above. The antibody solution is removed and washed three times with cold PBS before adding cell suspension. The cells are washed in R10 if proceeding directly to cell culture and stimulation. If performing CFSE staining to track cell proliferation, the cells are washed with PBS to remove any traces of proteins. The cells are pelleted by centrifuging for 5 minutes at 400 g at RT.

Optionally, the cells are stained with CFSE. The CFSE working solution is prepared by adding 2 μL of the stock to 1 mL of PBS (final concentration 10 μM). The working solution is pre-warmed at 37° C. before adding to the cell pellet. The supernatant is removed from the cell pellet. The appropriate volume of CFSE is added to achieve ~$10^7$ cells/mL and vortexed. The sample is incubated for 7 minutes in a 37° C. water bath. 1-2 mL cold FBS is added to stop the reaction, vortexed, and topped up with R10. The tubes are centrifuged for 5 minutes at 400 g. The supernatant is removed and resuspended in R10 at a density of $2.5 \times 10^5$ cells/mL.

The cells are cultured in the presence of the appropriate stimuli. Some extra wells are left with unstimulated CFSE-stained cells to be used as a compensation control at the time of analysis. Unstained PBMC provide an appropriate negative control. Human T cell subsets are efficiently expanded with anti-CD3/CD2/CD28 beads, IL-7 or IL-15, as depicted in FIGS. 14A-14L. NHP T cell subsets are expanded by stimulating with plate-bound anti-CD3 and soluble CD28 (final concentration: 1 μg/mL). Moreover, NHP CD8$^+$ T cell subsets, with the exception of $T_N$, are expanded in the presence of human IL-15. Anti-CD3/CD2/CD28 beads are used at a 1:2 bead-to-cell ratio to ensure optimal stimulation. IL-7 and IL-15 are both used at 25 ng/mL. However, antibody and cytokine concentrations are determined according to the experimental need. Optionally, cells are collected and stained for surface antigens as described above.

Helpful hints are described in Table 2.

TABLE 2

| Situation | Possible reason | Solution |
|---|---|---|
| Cell clumps after thaw | Excessive cell death | Include DNAse in thawing medium. If aggregates are still seen, sample is filtered over a 70 μm strainer |
| Compbeads aggregates | Sonication was not effective | Sonication time is increased to 10 min |
| Poor CCR7 staining | Presence of $NaN_3$ in the buffer | Buffer without $NaN_3$ is used |
| | Staining performed at RT | Cells are stained for CCR7 at 37° C. for 20 minutes in a separate step |

TABLE 2-continued

| Situation | Possible reason | Solution |
|---|---|---|
| Antibody aggregates are seen after staining | 2 minutes antibody mix centrifugation was not effective | Antibody mix is spun for 5-10 minutes before use |
| Low purity of sorted subsets | Poor separation of antigen expression due to very high initial cell number | Antibody concentration is increased in the mix |
| | Poor separation of antigens due to titration issues, fluorochrome spreading, etc. | Panel is tested carefully before use. FMO controls are checked to determine if compensation is correct and the presence of spreading errors. |
| CFSE dilution is not observed despite increase in cell number in culture | CFSE aliquot has expired or has been freezed/thawed multiple times | A new batch of CFSE is used and tested on fresh PBMC stimulated with anti-CD3/CD2/CD28 beads for 4 days before use |
| Sorted cells do not expand after stimulation | Expired anti-CD3/CD2/CD28 beads or cytokines Cytokine concentration is too low | A new batch of anti-CD3/2/38 beads or cytokines is used Cytokines are titrated to optimize concentration |

The panels indicated here provide the correct identification of human and NHP primate $CD4^+$ and $CD8^+$ $T_{SCM}$ cells (FIGS. 11A-11Z). Naïve-like cells, which include both true naïve cells as well as $T_{SCM}$ cells, are identified using at least three markers and are defined here as $CD45RO-CCR7^+$ $CD62L^+$ in humans and as $CD45RA^+$ $CCR7^+$ $CD28^+$ in rhesus macaques (Table 1, Panel #1 and Panel #3, respectively). In humans, if using cryopreserved cells, CD62L is replaced by a different marker (e.g. CD27, Table 1, Panel #2). Within naïve-like cells, a subset expressing CD95, the $T_{SCM}$ population, is identified (FIGS. 11A-11V). Adding an MHC class I tetramer allows the identification of antigen-specific $T_{SCM}$ cells by using the same gating strategy.

The expected frequency of $T_{SCM}$ cells is approximately 2-4% of the total $CD4^+$ and $CD8^+$ T cell populations and does not change appreciably with the age of the donor. The expected yield after sorting is 1 $CD4^+$ $T_{SCM}$ cell per every 250 PBMC and 1 $CD8^+$ $T_{SCM}$ cell per every 500-1,000 PBMC.

For human PBMC, improved identification of the $T_{SCM}$ population is achieved by including CD58 or CD122 in the staining panel, as these markers are differentially expressed in $T_{SCM}$ vs. $T_N$ (FIGS. 13A-13F). In rhesus macaques, adding CXCR3 ensures better separation of the $CD8^+$ $T_{SCM}$ subset, as virtually all $CD8^+$ $T_{SCM}$ cells are also $CXCR3^+$ (FIGS. 11E-11V).

Bulk $T_{SCM}$ cells, as well as other subsets, are sorted by flow cytometry at high purity for subsequent genetic analysis, in vitro expansion and genetic manipulation. Indeed, stimulation with anti-CD3/CD2/CD28 antibody-coated beads or homeostatic cytokines induces cell cycle entry, thus allowing the transduction with retroviral vectors (Cavalieri et al., Blood, 102: 497-505 (2003)). Genetically-modified cells are then be utilized for adoptive transfer experiments.

Effective $T_{SCM}$ expansion in vitro is achieved by stimulating with anti-CD3/CD2/CD28 antibody-coated beads (human), plate-bound anti-CD3 and soluble anti-CD28 (NHP) or the homeostatic cytokines IL-7 and IL-15. In vitro, $CD4^+$ T cells are preferentially expanded by IL-7 while CD8+ T cells respond to both IL-7 and IL-15. A differential response of human $T_N$ and memory cells is seen with these stimuli, as depicted in FIGS. 14A-14L. Thus, expansion conditions are adjusted before proceeding with the experiment. A combination of both IL-7 and IL-15 is used to maximize T cell stimulation (Cavalieri et al., Blood, 102: 497-505 (2003)). Stimulation through CD3, CD2 and CD28 expands cells much more efficiently than homeostatic cytokines but also causes a drastic change in the cell phenotype, including downregulation of CD45RA, CCR7 and CD62L with progressive proliferation as measured by CFSE dilution. Thus, the appropriate stimuli are chosen depending on the application.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing an isolated T memory stem cell population, the method comprising
    (a) isolating lymphocytes from a mammal; and
    (b) sorting the lymphocytes using flow cytometry into a population comprising a phenotype comprising
        (i) CD95+, CD45RO−, and CCR7+; and
        (ii) CD62L+or one or more of CD27+, CD28+, CD45RA+, and CD127+, to produce an isolated T memory stem cell population.

2. The method of claim 1, wherein (b) comprises sorting the lymphocytes into a population comprising a phenotype further comprising any one or more of CD58+, CD122+, CD3+, CD4+, and CD8+.

3. The method of claim 1, further comprising expanding the numbers of T memory stem cells in vitro.

4. The method of claim 1, further comprising transducing the isolated T memory stem cells with a nucleotide sequence encoding a chimeric antigen receptor (CAR) or a T cell receptor (TCR).

5. The method of claim 4, wherein the CAR or TCR has antigenic specificity for a cancer antigen or a viral antigen.

6. The method of claim 2, further comprising transducing the isolated T memory stem cells with a nucleotide sequence encoding a CAR or a TCR.

7. The method of claim 6, wherein the CAR or TCR has antigenic specificity for a cancer antigen or a viral antigen.

8. The method of claim 1, wherein the isolated T memory stem cells in the population produced by the method do not have a CD161$^+$phenotype.

9. The method of claim 1, wherein the isolated T memory stem cells in the population produced by the method do not have a IL-18Rα$^+$phenotype.

10. The method of claim 1, wherein the isolated T memory stem cells in the population produced by the method are not mucosal-associated invariant T cells (MAITs).

11. The method of claim 1, wherein the isolated T memory stem cells in the population produced by the method do not express RORC.

12. The method of claim 1, wherein the isolated T memory stem cells in the population produced by the method do not express IL17A.

* * * * *